US 8,194,234 B2

(12) United States Patent
Hopke et al.

(10) Patent No.: US 8,194,234 B2
(45) Date of Patent: Jun. 5, 2012

(54) METHODS FOR DETECTING PARTICLES IN AEROSOL GAS STREAMS

(75) Inventors: Philip Karl Hopke, Potsdam, NY (US); Jeffrey Lawrence Ambs, Foxboro, MA (US)

(73) Assignee: Thermo Fisher Scientific Inc., San Jose, CA (US)

( * ) Notice: Subject to any disclaimer, the term of this patent is extended or adjusted under 35 U.S.C. 154(b) by 0 days.

(21) Appl. No.: 12/824,726

(22) Filed: Jun. 28, 2010

(65) Prior Publication Data

US 2010/0263731 A1   Oct. 21, 2010

Related U.S. Application Data

(62) Division of application No. 11/615,672, filed on Dec. 22, 2006, now Pat. No. 7,777,867.

(51) Int. Cl.
*G01N 37/00* (2006.01)
(52) U.S. Cl. .......................................... 356/37; 73/28.01
(58) Field of Classification Search ................. 73/23.36, 73/23.42, 28.01, 280; 356/37
See application file for complete search history.

(56) References Cited

U.S. PATENT DOCUMENTS

| 2,684,008 | A | 7/1954 | Vonnegut |
| 3,117,841 | A | 1/1964 | Van Luik, Jr. et al. |
| 3,011,387 | A | 12/1964 | Johnson |
| 3,592,546 | A | 7/1971 | Gussman |
| 3,694,085 | A | 9/1972 | Rich |
| 3,806,248 | A | 4/1974 | Sinclair |
| 4,293,217 | A | 10/1981 | Bird, Jr. et al. |
| 4,449,816 | A | 5/1984 | Kohsaka et al. |
| 4,790,650 | A | 12/1988 | Keady |
| 4,950,073 | A | 8/1990 | Sommer |
| 5,011,281 | A | 4/1991 | Harris |
| 5,076,097 | A | 12/1991 | Zarrin et al. |
| 5,239,356 | A | 8/1993 | Holländer et al. |
| 5,247,842 | A | 9/1993 | Kaufman et al. |
| 5,519,490 | A | 5/1996 | Nakata et al. |
| 5,872,622 | A | 2/1999 | Schildmeyer |

(Continued)

FOREIGN PATENT DOCUMENTS

WO          97/33155          9/1997

OTHER PUBLICATIONS

Agarwal et al., "Continuous Flow, Single-Particle-Counting Condensation Nucleus Counter," J. Aerosol Sci., vol. 11, pp. 343-357.

(Continued)

*Primary Examiner* — John Fitzgerald
(74) *Attorney, Agent, or Firm* — Gordon Stewart

(57) ABSTRACT

Turbulent mixing condensation devices, methods, and systems adapted to condense a working fluid on particles from a sample gas to enlarge the particles for subsequent detection are provided. The device includes a vapor generator adapted to produce a working-fluid saturated carrier gas and a condensation chamber. The working-fluid saturated carrier gas is mixed with a sample gas containing particles to be detected and is then introduced to the condensation chamber. The operating conditions are controlled to enhance the condensation of the working fluid on the particles. The particles are typically forwarded to a particle detection device to detect at least one characteristic, for example, the size, of the particles. The flow of carrier gas to the vapor generator may be regulated to vary the degree of saturation of the carrier gas with working fluid.

23 Claims, 11 Drawing Sheets

U.S. PATENT DOCUMENTS

| | | | |
|---|---|---|---|
| 5,903,338 | A | 5/1999 | Mavliev et al. |
| 6,469,780 | B1 | 10/2002 | McDermott et al. |
| 6,469,781 | B1 | 10/2002 | Katz et al. |
| 6,529,272 | B2 | 3/2003 | Flagan et al. |
| 6,567,157 | B1 | 5/2003 | Flagan et al. |
| 6,712,881 | B2 | 3/2004 | Hering et al. |
| 6,829,044 | B2 | 12/2004 | Liu |
| 7,363,828 | B2* | 4/2008 | Liu ............................ 73/863.03 |
| 7,407,531 | B2* | 8/2008 | Flagan et al. .................... 95/154 |
| 7,777,867 | B2* | 8/2010 | Hopke et al. ..................... 356/37 |
| 2003/0199100 | A1 | 10/2003 | Wick |
| 2006/0144126 | A1 | 7/2006 | O'Brien et al. |
| 2006/0146327 | A1 | 7/2006 | Wang et al. |
| 2011/0056273 | A1* | 3/2011 | Gorbunov et al. ........... 73/28.01 |

OTHER PUBLICATIONS

Ankilov et al., "Particle Size Dependent Response of Aerosol Counters," Atmospheric Research 62, pp. 209-237 (2002).

Bricard et al., "Counting of Condensation Nuclei at Low Pressures: Its Application to Photolysis of Gaseous Impurities in the Stratosphere," U.S. Department of Transportation Third Conference on CIAP, Feb. 1974, pp. 168-172.

Cadle et al., "Stratospheric Aitken Particles Near the Tropopause," Geophysical Research Letters vol. 2 No. 8 (Aug. 1975), pp. 329-332.

Gallar et al., "A Variable Supersaturation Condensation Particle Sizer," Aerosol Science and Technology 40 pp. 431-436 (2006).

Kim et al., "Performance Evaluation of an Improved Particle Size Magnifier (PSM) for Single Nanoparticle Detection," Aerosol Science and Technology 37, pp. 791-803 (2003).

Kousaka et al., "Development of a Mixing Type Condensation Nucleus Counter," J. Aerosol Sci. vol. 13, No. 3, pp. 231-240 (1982).

Lee et al., "Comparison of Experimental and Theoretical Heterogeneous Nucleation on Ultrafine Carbon Particles," J. Phys. Chem. B 2003, 107, pp. 13813-13822.

Mavliev et al., "Evaluation of Turbulent Mixing-Type CNC at 3-40 NM Range," AAAR '96 Abstracts p. 149 (1996).

Mavliev et al., "Experimental Studies of Heterogeneous Nucleation in the Turbulent Mixing Condensation Nuclei Counter," J. Phys. Chem. B 2004, 108, pp. 4558-4564.

Mavliev et al., "A Transition from Heterogeneous to Homogeneous Nucleation in the Turbulent Mixing CNC," Aerosol Science and Technology 35, pp. 586-595 (2001).

Mavliev et al., "A Transition From Heterogeneous to Homogeneous Nucleation in the Turbulent Mixing CNC," J. Aerosol Sci. vol. 30, Suppl. 1, pp. S31-S32 (1999).

Mavliev, "Turbulent Mixing Condensation Nucleus Counter," Atmospheric Research 62, pp. 303-314 (2002).

McDermott et al., "Counting Efficiency of an Improved 30-A Condensation Nucleus Counter," Aerosol Science and Technology 14, pp. 278-287 (1991).

McMurry, Peter H. "The History of Condensation Nucleus Counters," Aerosol Science and Technology 33, pp. 297-322 (2000).

Okuyama et al., "Condensational Growth of Ultrafine Aerosol Particles in a New Particle Size Magnifier," Aerosol Science and Technology pp. 353-366 (1984).

Okuyama et al., "Homogeneous Nucleation by Continuous Mixing of High Temperature Vapor with Room Temperature Gas," Aerosol Science and Technology 6, pp. 15-27 (1987).

Rosen et al., "Stratospheric Condensation Nuclei," Report No. Ap-61 (supported by NASA under Grant NSG-7349 and NAG-2-65), 32 pages (1981).

Sgro et al., "A Simple Turbulent Mixing CNC for Charged Particle Detection Down to 1.2 nm," Aerosol Science and Technology 38, pp. 1-11 (2004).

Simon et al., "Continuous Automated Measurement of the Soluble Fraction of Atmospheric Particulate Matter," Analytical Chemistry vol. 67, No. 1, pp. 71-78 (Jan. 1, 1995).

Sinclair et al., "A Continuous Flow Condensation Nucleus Counter," Aerosol Science vol. 6, pp. 1-7 (1975).

Stolzenburg et al., "An Ultrafine Aerosol Condensation Nucleus Counter," Aerosol Science and Technology 14, pp. 48-65 (1991).

Strum et al., "Microphysical Measurements of Fog Formed in a Turbulent Jet," Aerosol Science and Technology 16, pp. 151-165 (1992).

Wilson et al., "The Function and Response of an Improved Stratospheric Condensation Nucleus Counter," Journal of Geophysical Research, vol. 88, No. C11, pp. 6781-6785.

Material Safety Data Sheet for "FC-43 Fluorinert Brand Electronic Liquid." 3M Company, 2005.

Material Safety Data Sheet for "FC-84 Fluorinert Brand Electronic Liquid." 3M Company, 2007.

Material Safety Data Sheet for "FC-72 Fluorinert Brand Electronic Liquid." 3M Company, 2005.

International Search Report for corresponding PCT application PCT/US07/88640, mailed May 2, 2008.

International Preliminary Report on Patentability for corresponding PCT application No. PCT/US2007/088640, mailed on Jul. 2, 2009.

Restriction Requirement for U.S. Appl. No. 11/615,672, mailed Mar. 24, 2009.

Non-Final Office Action for U.S. Appl. No. 11/615,672, mailed Jul. 6, 2009.

* cited by examiner

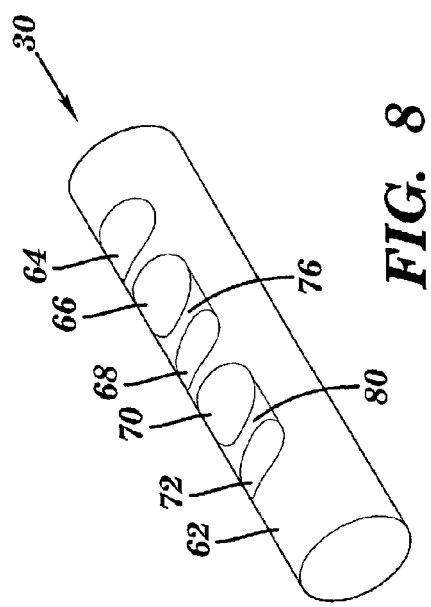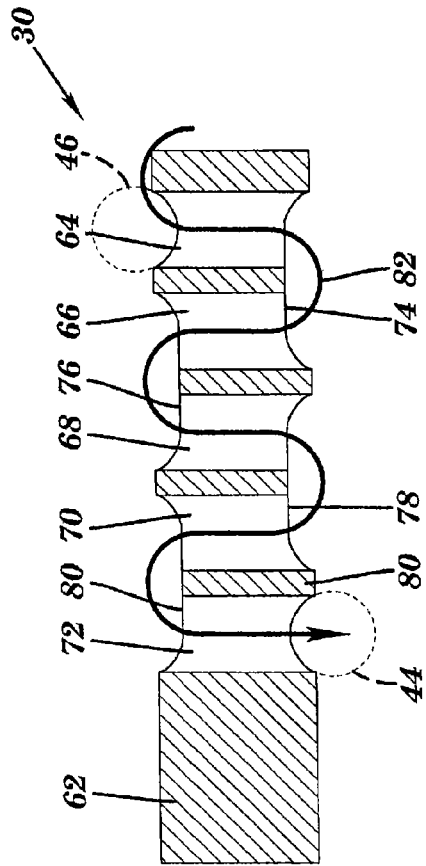

METHODS FOR DETECTING PARTICLES IN AEROSOL GAS STREAMS

This application is a divisional application of U.S. patent application Ser. No. 11/615,672, filed on Dec. 22, 2006, now U.S. Pat. No. 7,777,867, the entire contents of which is incorporated herein by reference in its entirety.

TECHNICAL FIELD

The present invention provides devices, methods, and systems for condensing fluids onto particles in gases to produce enlarged fluid-particle structures that can be more readily detected. Specifically, aspects of the present invention provide improved turbulently mixed condensation nuclei counters and systems that can be used to monitor indoor and outdoor air quality.

BACKGROUND OF THE INVENTION

One of the major hypotheses that has recently been proposed for the cause of the observed effect of particulate matter on human health is that high numbers of ultrafine particles (for example, particles, diameters less than 0.1 µm) are more problematic than the particle mass that is now the basis of the National Ambient Air Quality Standards. For example, significant associations of elevated cardiovascular and respiratory disease mortality with various fine (and ultrafine) particle indices have been found in one study based in Erfurt, Germany. Specifically, significant associations were found between mortality and ultrafine particle number (NC), ultrafine particle mass (MC), fine particle mass or $SO_2$ concentrations. The correlation between MC 0.01-2.5 and NC 0.01-0.1 is only moderate, suggesting that it may be possible to partially separate effects of ultrafine and fine particles. Thus, measurements of the ultrafine particle concentrations as well as particle mass are needed to help provide more data to examine these relationships.

In addition, there are a variety of particle counting needs in industrial settings. With the increased emphasis on nanometer sized particles for the production of nanostructured materials, particle counters can be important in process control. There are currently only a limited number of instruments available to make such measurements.

One method or device that has shown to be an effective means of detecting such fine particles is the use of heterogeneous nucleation with a turbulent mixing condensation nuclei counter (that is, a "TMCNC"). In a TMCNC system, a gas (for example, air) containing the particles to be measured is turbulently mixed with a stream of air saturated with a condensable vapor so that the vapor cools and condensates, that is nucleates, onto the particles. The resulting droplets or nuclei then grow to a size whereby they can be effectively detected by, for example, light scattering. Although the concept of a TMCNC has been available for over 15 years (see for example, McMurry, 2000), the TMCNC has not been developed into a viable commercial instrument capable of particle detection down to 2 nanometers.

The Condensation Nuclei Counter (CNC), which grows primary particles (nuclei) up to a more easily detectable size, is one of the most widely used devices for studying particles below 0.1 micrometer (µm). A general description of CNC's is given in many books and reviews (for example, see Willeke and Baron, 1993 and McMurry, 2000). Several types of CNCs are used in researching aerosols, that is, suspensions of fine solid or liquid particles in a gas, typically, air. The main difference among these CNC designs is the way the devices produce supersaturation that leads to particle growth up to a predetermined size for subsequent detection. In an expansion-type CNC, supersaturation is generated by adiabatic cooling during pressure reduction. An expansion-type CNC is typically a batch instrument. Expansion-type CNCs have been used in atmospheric aerosol research for many years. A continuous CNC (for example, as disclosed by Agarwal and Sem, 1980) is widely used. In the continuous CNC, supersaturation is formed by cooling a laminar aerosol flow that is saturated with working fluid vapor. In the conductive cooling type continuous CNC the aerosol-containing sample is typically saturated with working fluid and then cooled whereby the working fluid condenses on the aerosol particles. However, one disadvantage of the conductive cooling CNC is its sensitivity to moisture in the sample gas. Moisture in the sample gas may also condense on the aerosol particles or otherwise interfere with the condensation of the working fluid and affect the measured particle count. Attempts to remove moisture from the sample gas typically can also remove aerosol particles, which hampers the accuracy of the particle measurements. Aspects of the present invention overcome this deficiency of the prior art.

The third type of CNC, known as a turbulent mixing CNC (or TMCNC), is based on turbulent mixing of a gas flow with particles with working fluid vapor. The TMCNC instrument has not yet been commercialized. One prior art TMCNC is described by Kogan and Burnashova (1960) and was further developed in different versions by Okuyama, et al. (1984); Ankilov, et al. (1991); Kousaka (1993); and Mavliev and Wang (1999). The major advantage of the TMCNC is the flexibility of generating supersaturation by simply mixing the aerosol flow and a separate gas flow saturated with the working fluid vapor.

The CNC is one of the most sensitive devices for detecting nanometer-size particles, for example, some CNC studies have reached a detection limit of 2-3 nanometers (nm) (Stolzenburg and McMurry, 1991; McDermont et al., 1991; Okuyama et al., 1984; Mavliev and Wang, 1999). In one commercially available CNC system that can detect 3 nm particles, the aerosol stream is directed through a capillary tube in order to align the particle stream within a small central zone of uniform saturation conditions. However, the capillary in this system is prone to problematic clogging when used to directly measure ambient aerosols and cleaning the capillary tube can be difficult.

The minimum detection efficiency of CNCs is very sensitive to the size of particles being detected (Makela, et al., 1996). The detection efficiency may also be sensitive to the composition of the particle (Mavliev et al., 2001) and to the nature of the working fluid (Lee et al., 2003; Mavliev et al., 2004).

Although the CNC is primarily devoted to measuring the number concentration of particles, some prior art CNCs have been shown to be able to measure size distribution of particles, for example, of nanometer-sized particles. In one prior art system, the size distribution of nuclei can be measured by means of changing the CNC's sensitivity (McDermont et al. 1991) and by means of measuring the size of grown particles (Ahn and Liu, 1990; Rebours, et al., 1996; Saros, et al., 1996). One prior art method is based on the fact that the growth of smaller particles is delayed because of the Kelvin effect that results in the final size of particles being dependent on initial nucleus size. However, these prior art devices provide unsatisfactory size resolution and their operational range is limited to a range of 3-10 nm. In addition, in some of these prior art systems, the growth time for particles of the same size depends strongly on spatial uniformity of supersaturation.

For most continuous flow CNCs, the spatial distribution of supersaturation is not uniform because of the use of diffusive cooling in the laminar flow (Stolzenburg, 1988).

Moreover, some commercially available prior art CNCs were developed as laboratory research tools or to monitor clean rooms, and, as far as the present inventors know, no effort has yet been made to optimize their performance for ambient aerosol monitoring. For example, typically, the aerosol-laden air streams of such research CNCs are not conditioned in any way, nor is there any control or limitation of the introduction of large particles to these CNCs. In prior art ultrafine CNCs, large particles can clog the device, for example, the capillaries in such devices. In addition, in prior art systems there is typically no control of temperature and humidity in the inlet stream and both temperature and humidity can produce some variability in the instrumental response. These deficiencies in the prior art devices cause problems when using a CNC for ambient particle monitoring.

In addition, prior art CNCs typically use n-butanol as the working fluid. However, butanol is toxic, flammable, has a noxious odor, and is thus undesirable in a commercially-available device that may readily experience human contact, operation, and servicing.

Thus, in view of the deficiencies and disadvantages of prior art CNCs, there is a need for an improved stand-alone TMCNC aerosol particle counter that will provide improved sensitivity, for example, for particle sizes down to the order of about 2 nm, well-defined inlet characteristics, robust design, consistent and reproducible performance, and employ a working fluid that is less offensive and less dangerous to humans. Aspects of the present invention address these and other deficiencies of the prior art while providing improved detection efficiency, greater ease of use, and adaptability for use in ambient gas particulate measurements.

SUMMARY OF THE INVENTION

Aspects of the present invention provide condensation devices and condensation nuclei counters and methods for operating such devices that address many of the disadvantages and deficiencies of the prior art. For example, one aspect of the invention is a turbulent mixing condensation device adapted to condense a working fluid on particles from a sample gas to enlarge the particles, the condensation device including a vapor generator which includes a working fluid chamber containing a level of the working fluid wherein a carrier gas directed through the working fluid chamber absorbs at least some working fluid to form a vapor containing working fluid; and a carrier gas chamber containing carrier gas; a vapor mixing device adapted to mix the vapor containing working fluid from the working fluid chamber with the carrier gas from the carrier gas chamber to produce a mixture of working fluid and carrier gas; and a condensation chamber including an inlet adapted to receive the mixture of working fluid and carrier gas; means for turbulently mixing the sample gas containing particles with the mixture to produce a particle-containing gas; a condensation tube adapted to receive the particle-containing gas and promote condensation of the working fluid on at least some of the particles to produce enlarged particles; and an outlet for a gas containing enlarged particles.

Another aspect of the invention is a method for detecting a characteristic of particles in a sample, the method including passing a first stream of a carrier gas over a working fluid wherein the carrier gas absorbs at least some of the working fluid to provide a vapor containing working fluid; mixing the vapor containing working fluid with a second stream of carrier gas to produce a mixture of working fluid and carrier gas at a first temperature; introducing the sample gas to the mixture, the sample gas containing particles and having a second temperature lower than the first temperature, to produce a particle-containing gas having a third temperature, lower than the first temperature; condensing at least some of the working fluid in the particle-containing gas onto at least some of the particles to produce enlarged particles; and detecting the characteristic of at least some of the enlarged particles.

Another aspect of the invention is a system for detecting a characteristic of particles in a sample gas, the system including the turbulent mixing condensation device as described above and a particle detector adapted to receive the gas containing enlarged particles from the outlet of the condensation chamber and detect the characteristic of at least some of the enlarged particles. In one aspect, the system further comprises means for introducing at least one of the working fluid and the carrier gas to the vapor generator at super atmospheric pressure, for example, using a pump, a compressor, or a blower.

Another aspect of the invention is a method for detecting a characteristic of particles of varying size in a sample gas, the method including introducing a working fluid to a carrier gas to provide a first mixture of working fluid and carrier gas having a first saturation ratio; introducing the sample gas to the first mixture, the sample gas containing particles, to produce a first particle-containing gas; condensing at least some of the working fluid from the first particle-containing gas onto at least some of the particles in the sample gas stream having a first size to produce first enlarged particles; detecting the characteristic of at least some of the first enlarged particles; introducing the working fluid to the carrier gas to provide a second mixture of working fluid and carrier gas having a second saturation ratio, different from the first saturation ratio; introducing the sample gas to the second mixture to produce a second particle-containing gas; condensing at least some of the working fluid from the second particle-containing gas onto at least some of the particles in the sample gas stream having a second size, different from the first size, to produce second enlarged particles; and detecting the characteristic of at least some of the second enlarged particles.

A still further aspect of the invention is a method for detecting a characteristic of particles in a sample gas, the method including dehumidifying a carrier gas to remove at least some moisture from the carrier gas; introducing the dehumidified carrier gas to a working fluid to provide a mixture of carrier gas and working fluid; introducing the sample gas containing particles to the mixture to produce a particle-containing gas; condensing at least some of the working fluid onto at least some of the particles to produce enlarged particles; and detecting the characteristic of at least some of the enlarged particles. According to aspects of the invention, the enlarged particles produced contain less condensed water than particles produced by a method practiced without dehumidifying the carrier gas.

Another aspect of the invention is a condensation apparatus adapted to condense a working fluid on particles from a sample gas to enlarge the particles, the condensation apparatus including a carrier gas dehumidifier adapted to remove at least some moisture from a carrier gas; a vapor generator adapted to introduce at least some working fluid to the carrier gas to produce a mixture containing working fluid and carrier gas; means for mixing the sample gas containing particles with the mixture to produce a particle-containing gas; a condensation chamber adapted to promote condensation of at least some of the working fluid onto at least some of the particles to produce enlarged particles; and an outlet for a gas containing enlarged particles.

A further aspect of the invention is a method for detecting a characteristic of particles in a sample gas, the method including introducing a carrier gas to a working fluid to provide a mixture of carrier gas and working fluid; introducing the sample gas containing particles to the mixture to produce a particle-containing gas; condensing at least some of the working fluid onto at least some of the particles in the particle-containing gas to produce enlarged particles; detecting the characteristic of at least some of the enlarged particles; and recovering at least some of the working fluid from particle-containing gas.

Another aspect of the invention is a condensation apparatus adapted to condense a working fluid on particles from a sample gas to enlarge the particles, the condensation apparatus including a vapor generator adapted to introduce working fluid to a carrier gas to produce a mixture of working fluid and carrier gas; means for mixing the sample gas with the mixture to produce a particle-containing gas; a condensation chamber adapted to promote condensation of at least some of the working fluid onto at least some of the particles to produce enlarged particles; a particle detector adapted to detect at least one characteristic of the enlarged particles; and means for recovering at least some of the working fluid from the particle-containing gas. In one aspect, the means for recovering may be a heat exchanger containing a cooler fluid.

Another aspect of the invention is a method for detecting a characteristic of particles in a sample gas, the method including injecting a working fluid into a carrier gas; mixing the carrier gas and the working fluid to provide a mixture having a predetermined degree of working fluid saturation; introducing the particle-containing sample gas to the mixture; condensing the working fluid on at least some of the particles to produce enlarged particles; and detecting the characteristic of at least some of the enlarged particles. The injecting may be practiced by providing a fine jet or a fine mist of working fluid to the carrier gas.

A still further aspect of the invention is a condensation device adapted to condense a working fluid on particles in a sample gas to enlarge the particles, the condensation device including a vapor generator comprising a working fluid chamber having a working fluid inlet and a carrier gas inlet; means for injecting the working fluid into the working fluid chamber through the working fluid inlet; a mixing device adapted to mix the working fluid with the carrier gas to produce a mixture of working fluid and carrier gas; and a condensation chamber including means for introducing the sample gas containing particles to the mixture to produce a particle-containing gas; a condensation tube adapted to promote condensation of the working fluid on at least some of the particles to produce enlarged particles; and an outlet for a gas containing enlarged particles.

These and other aspects, features, and advantages of this invention will become apparent from the following detailed description of the various aspects of the invention taken in conjunction with the accompanying drawings.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

FIG. 8 is a perspective view of a mixing baffle according to one aspect of the invention.

FIG. 9 is a side elevation view, partially in cross section of the mixing baffle shown in FIG. 8.

DETAILED DESCRIPTION OF THE INVENTION

Figure 1:
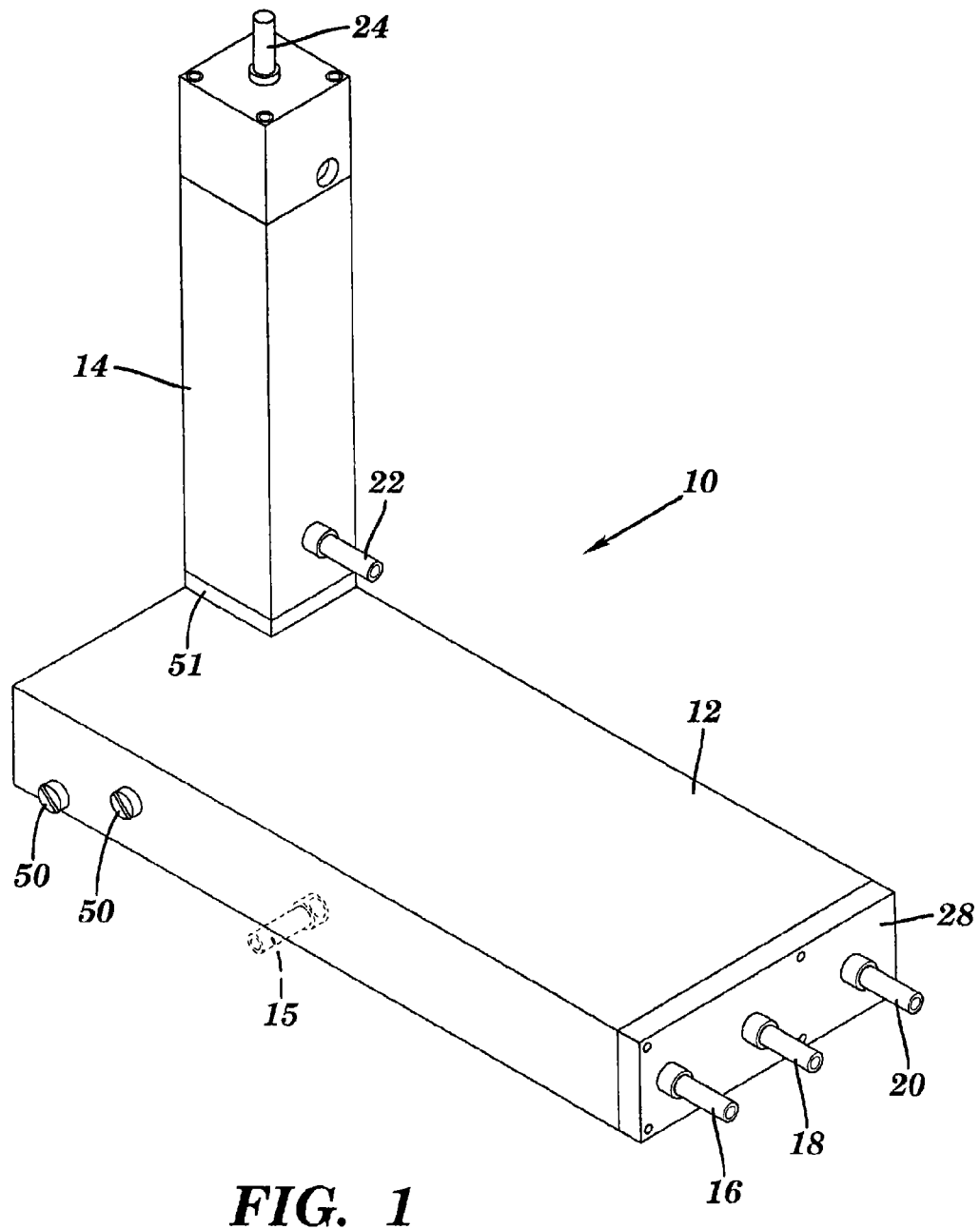
FIG. 1 is a perspective view of a turbulent mixing condensation device according to one aspect of the invention.
Figure 2:
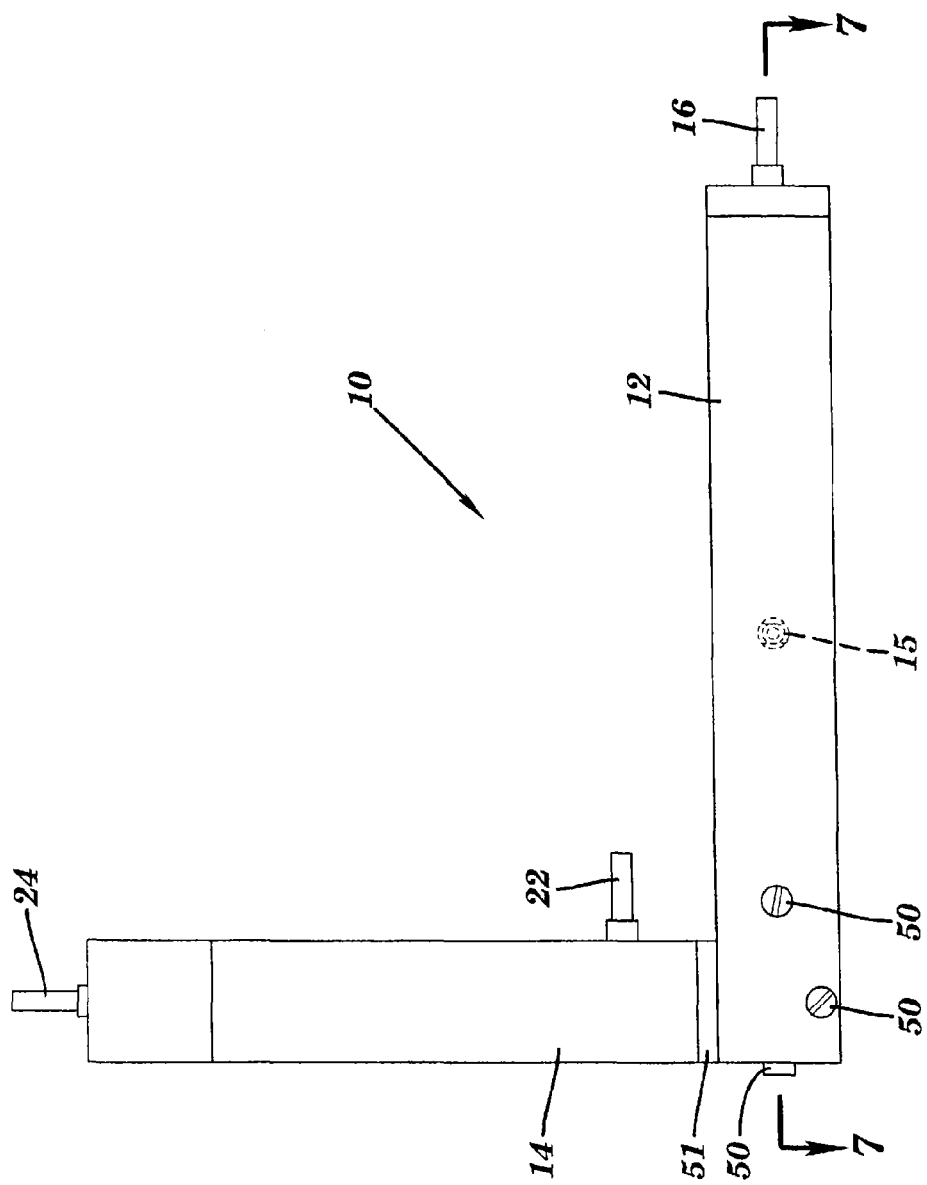
FIG. 2 is a front elevation view of the turbulent mixing condensation device shown in FIG. 1.
Figure 3:
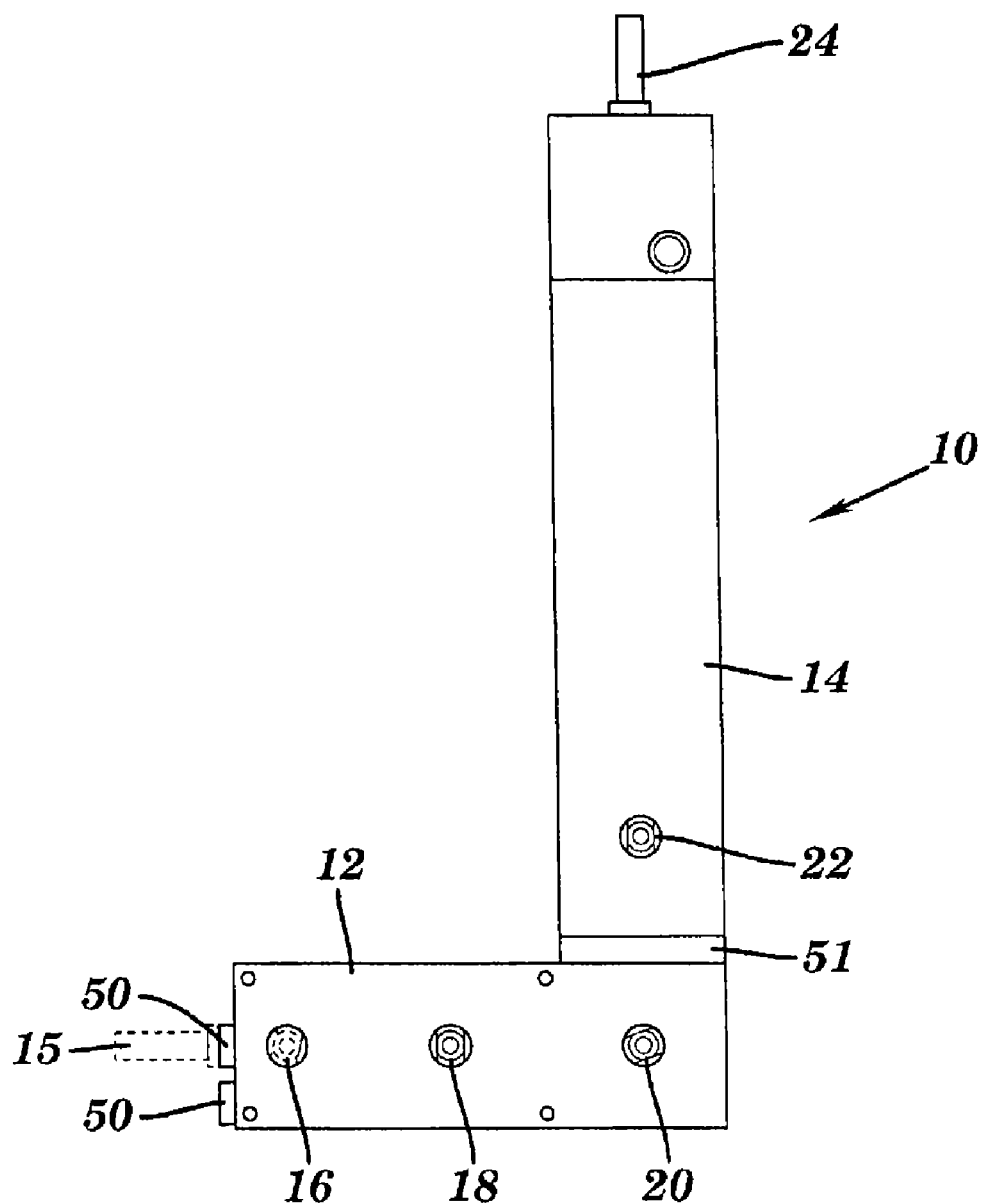
FIG. 3 is a right side elevation view of the turbulent mixing condensation device shown in FIG. 1.
Figure 4:
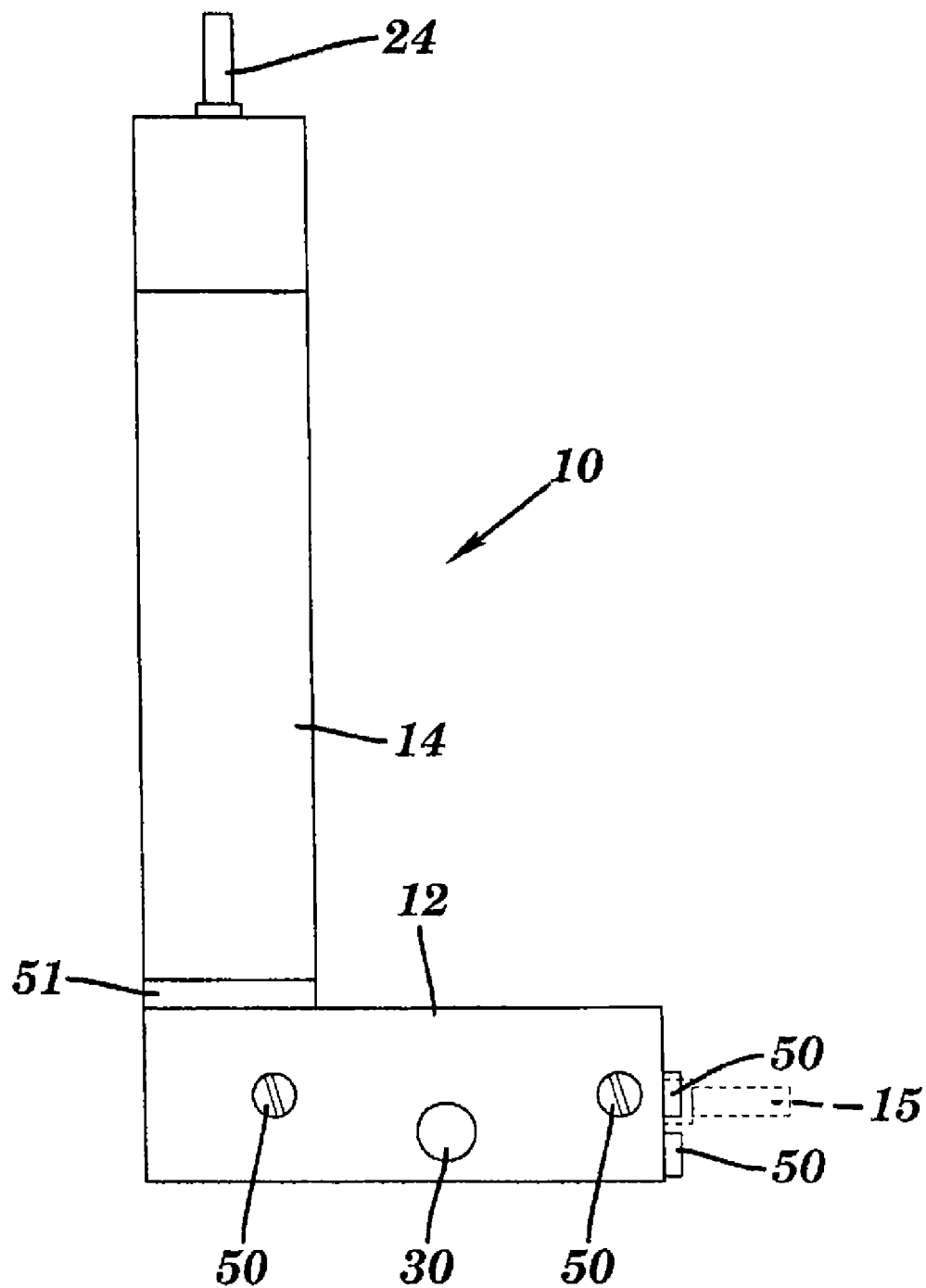
FIG. 4 is a left side elevation view of the turbulent mixing condensation device shown in FIG. 1.
Figure 5:
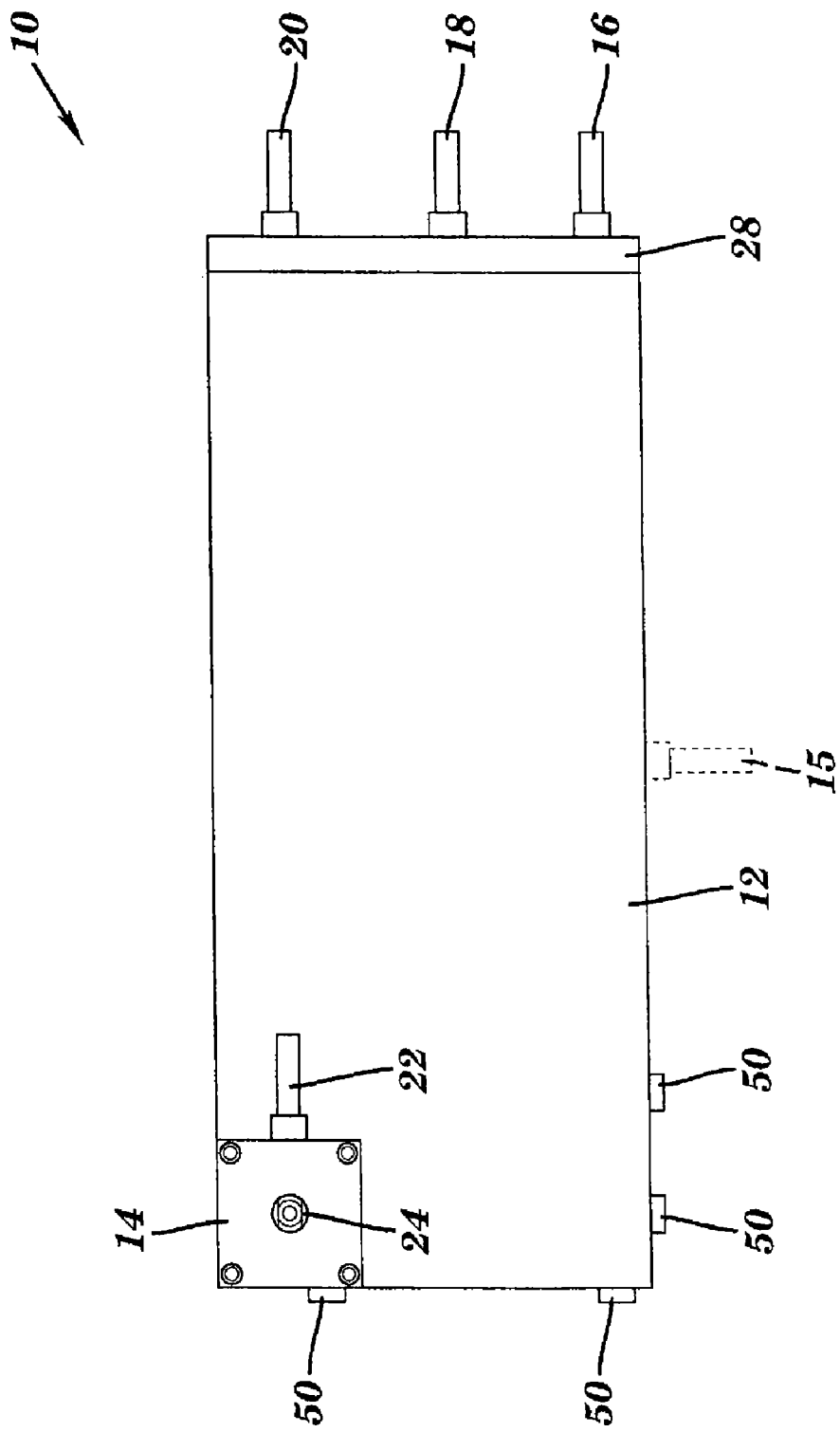
FIG. 5 is a top plan view of the turbulent mixing condensation device shown in FIG. 1.

FIG. 1 is a perspective view of a turbulent mixing condensation device 10 according to one aspect of the invention. Device 10 includes a vapor generator 12 and a condensation chamber 14. According to aspects of the invention, vapor generator 12 is adapted to generate a vapor from a liquid working fluid introduced to one or more input nozzles 16, 18, and/or 20, and transfer the vapor to condensation chamber 14 where the vapor is mixed with a sample gas having particles introduced via nozzle 22. In one aspect, condensation device 10 may include one or more fluid injection nozzles 15 (shown in phantom) to supplement or replace input nozzles 16, 18, and 20. In condensation chamber 14, the working fluid vapor condenses on the particles introduced with the sample gas to create enlarged particles, or nuclei. The vapor having the enlarged particles is then discharged from outlet 24 to a particle-detecting device (not shown), for example, an optical particle counter, to detect at least one characteristic of the particles.

FIG. 2 is a front elevation view of device 10 shown in FIG. 1; FIG. 3 is a right side elevation view of device 10; FIG. 4 is a left side elevation view of device 10; FIG. 5 is a top plan view of device 10; and FIG. 6 is an exploded perspective view of device 10 shown in FIG. 1. Though not shown in these figures, device 10 is typically covered with some form of thermal insulation to facilitate maintenance of a desired operating temperature, for example, to minimize heat loss from vapor generator 12 and heat gain to condensation chamber 14. The insulation is omitted from these figures to facilitate illustration of device 10 and its components. The insulation may comprise a styrofoam insulation, among other types of insulation.

As shown most clearly in FIG. 6, vapor generator 12 includes a main body 26 having a series of cavities and passages (discussed below), an end plate 28, and mixing device 30. FIG. 7 is a cross sectional view of main body 26 of vapor generator 12 as viewed along lines 7-7 in FIG. 2 according to one aspect of the invention. As shown in FIG. 7, main body 26 typically includes at least one internal chamber 32, for example, the three internal chambers 32, 34, and 36 shown. Internal chambers 32, 34, and 36 may be fed by nozzles 20, 18, and 16, respectively, shown in FIGS. 1-6. The temperature of vapor generator 12 may be regulated by some form of heating means or heating device (not shown), for example, a thermo-electric heater or a heat exchanger. The operation of the heating means may be regulated by a feedback control system having one or more temperature sensors mounted to or in vapor generator 12.

According to one aspect of the present invention, one or more internal chambers 32, 34, and 36 may be provided with a working fluid, that is, a fluid that is capable of forming a vapor that can be condensed on particles in the sample gas stream. One of chambers 32, 34, and 36 may be typically partially filled with a working fluid, that is, the chamber may comprise a working fluid chamber, whereby a surface of working fluid is provided in one of the chambers. According to aspects of the invention, a gas, that is, a carrier gas, may be passed over the working fluid surface causing at least some of the working fluid to evaporate into the carrier gas and be transported by the carrier gas to condensation chamber 14.

According to aspects of the invention, various working fluids may be used, for example, depending upon the nature of the sample gas and/or the nature of the particles in the sample gas stream upon which the working fluid condenses. In one aspect, the working fluid may be water, for example, distilled water; an alcohol, such as butanol; or a perfluoro compound, such as, FC-72, though other types of working fluids may be used. In another aspect, the working fluid may be a liquid containing perfluoro compounds, for example, one or more of the liquids sold by the 3M Company under the trade name Flourinert, such as FC-43, FC-72, or FC-84, the Material Safety Data Sheets (MSDS) for each of which are included by reference herein, or their derivatives or equivalents. In one aspect, the working fluid comprises a fluid that can be readily or more economically recovered for re-use.

At least one of chambers 32, 34, and 36 may be devoid of working fluid, that is, contains no working fluid, but is filled with a carrier gas. Such a chamber may comprise a carrier gas chamber. According to this aspect, a carrier gas is any gas that can be used as a conveying medium for transferring the vaporous working fluid from vapor generator 12 to condensing chamber 14. The carrier gas may be nitrogen; an inert gas, for example, argon; air, for example, ambient air; or mixtures thereof. In one aspect of the invention, the carrier gas may be conditioned to optimize the operation of the device, for example, the carrier gas may be filtered, temperature controlled, and/or humidity controlled, among other conditioning processes. For example, according to one aspect of the invention, the carrier gas may be dehumidified and/or filtered to remove moisture and/or contaminants. In contrast to conductive cooling type CNCs, where the carrier gas comprises the sample gas, according to aspects of the present invention, the dehumidifying and/or filtering of the carrier gas does not interfere with the aerosol particle content of the sample gas.

In another aspect, at least one of chambers 32, 34, and 36 may be a reservoir for the carrier gas or the working fluid. For example, at least one of chambers 32, 34, and 36 may be a reservoir for the working fluid or carrier gas whereby the working fluid or carrier gas is maintained at a desired temperature and/or pressure prior to being introduced to another of the chambers 32, 34, and/or 36.

The working fluid and carrier gas may be introduced to chambers 32, 34, and 36 through one or more nozzles 16, 18, and 20 mounted in end plate 28 shown in FIGS. 1 and 2. Nozzles 16, 18, and 20 may be conventional fluid (that is, gas or liquid) nozzles or specially-designed fluid nozzles.

In the aspect of the invention shown in FIG. 7, vapor generator body 26 includes three internal chambers 32, 34, and 36. In aspects of the present invention, vapor generator body 26 may include 4 or more chambers or 6 or more chambers, for example, two sets of chambers 32, 34, and 36.

The working fluid may be transferred to and from chambers 32, 34, and 36 via external conduits, for example, via nozzles 16, 18, and 20. Working fluid may also be transferred between chambers 32, 34, and 36 by means of a "wicking" material, that is, a material or fabric that functions to draw fluid from one chamber into another chamber by means of capillary action. For example, as shown in FIGS. 6 and 7, a wicking material 41 may be positioned whereby at least some of a first end of the wicking material 41 is positioned in chamber 34 (for example, a working fluid reservoir chamber) and at least some of a second end of the wicking material 41 may be positioned in chamber 36 (for example, a carrier gas chamber) whereby working fluid is readily "wicked" to chamber 36 from chamber 34 when chamber 34 is supplied with sufficient working fluid. Wicking material 41 may be a cotton or felt material, or any other material that can transfer working fluid between two chambers. In addition, the working fluid may be transferred between chambers 32, 34, and 36 by means of a porous medium, for example, a porous ceramic or a porous metal positioned between two of chambers 32, 34, and 36.

As shown in FIGS. 6 and 7, the end face 43 of vapor generator body 26 of vapor generator 12 may include counter bores or reliefs adapted to accommodate wicking material 41, and may include one or more sealing elements about chambers 32, 34, and 36, as needed. For instance, as shown in FIG. 6, face 43 may include a racetrack-shaped relief or depression 45 around the open ends of chambers 34 and 36 to provide a pathway for passing wicking material 41 between chambers 34 and 36. Depression 45 may also provide a recess for retaining a sealing element; for example, an o-ring or gasket, which seals the open ends of chambers 34 and 36 against end plate 28. Similarly the open end of chamber 32 may include a relief or counter bore 47 to provide a recess for retaining a sealing element, for example, an o-ring or gasket that seals the open end of chamber 32 against end plate 28.

As shown in FIG. 7, vapor generator 12 may also include one or more working fluid injection ports, such as port 35 shown in phantom in FIG. 7. Port 35 may be adapted to receive nozzle 15, shown in phantom in FIGS. 1-6. Though port 35 is shown as associated with internal chamber 36, one or more ports 35 may be associated with one or more of chambers 32, 34, and/or 36. In one aspect, nozzle 15 and port 35 may be used to supplement or replace the function of nozzles 16, 18, and 20. For example, in one aspect, working fluid may be introduced to chamber 36 via one or more ports 35 in addition to the working fluid introduced to chamber 36 from chamber 34, for example, via wicking material 41.

In another aspect, essentially all the working fluid may be introduced to chamber 36 via one or more ports 35, whereby little or no working fluid need be introduced from chamber 32 or 34. In one aspect, with the introduction and regulation of the flow of working fluid to chamber 36 via port 35, chambers 32 and 34 may be eliminated whereby vapor generator 12 may comprise only a single internal chamber 36. Vapor generator 12 may also comprise two or more chambers 36 having individual fluid injection ports 35 therein. In another aspect of the invention, working fluid may also be injected into internal chamber 40 and mixed with a carrier gas by means of static mixing element 30 (discussed below) whereby no internal chambers 32, 34, or 36 may be necessary. Though port 35 in FIG. 7 is illustrated as located at approximately the mid length of chamber 36, one or more ports 35 may be positioned anywhere along the length or circumference of chamber 36. One or more ports 35 may be positioned adjacent to the open end of chamber 36, for example, adjacent to the outlet of nozzle 16 to enhance the mixing of the working fluid with the carrier gas introduced via nozzle 16, and/or to provide sufficient retention within chamber 36 to ensure adequate absorption or mixing of the working fluid into the carrier gas. Two or more ports 35 may be distributed along the length of chamber 36 and the flow of working fluid to the two or more ports 35 may be substantially uniform or may be varied as desired, for example, to provide a desired saturation ratio. In addition, aspects of the present invention having one or more ports 35 may allow for a more precise control of the introduction of working fluid to the carrier gas, for example, to provide a more accurate and controlled degree of saturation level and/or to provide for varying saturation levels, for instance, precise variation of saturation levels, among other advantages. A controller may be provided to control the flow of working fluid to the one or more ports 35, for example, one or more valves operated by a control system (for example, the controller 250 shown in FIG. 13) in response to a desired predetermined saturation level of the working fluid saturated vapor.

One advantage of introducing working fluid to saturation chamber 12 by means of fluid injection via one or more ports 35, for example, as needed to provide the desired saturation to the carrier, is that this may obviate the need to maintain fluid in vapor generator 12. This aspect of the invention can be particularly advantageous when device 10 is tipped, transported, shipped, or otherwise handled wherein fluids may leak from vapor generator 12 and potentially damage parts of device 10 or related devices, for example, potentially damage the optics in the particle detecting device—as is known in the art, optical devices can be very expensive and time consuming to inspect and clean. Typically, to avoid leakage and damage during handling, prior art devices are drained of working fluid before handling. According to aspects of the invention, no working fluid may be present in vapor generator 12 when device 10 is not in operation. Thus, there is little or no likelihood of working fluid leakage during handling.

In one aspect, the working fluid introduced by means of port 35 may be introduced in a variety of forms to enhance absorption and/or mixing into the carrier gas. For example, the working fluid may be introduced by means of a nozzle or orifice providing a fine jet of fluid or as a fine mist of fluid, for example, in a fashion similar to the way fuel is injected in automobile fuel injection systems. The working fluid may be introduced as a pressurized flow of working fluid, for example, having a pressure of at least 5 psig. The shape and nature of the introduction of the working fluid to chamber 36 may be dependent upon the properties of the working fluid (for example, its viscosity) and the carrier gas (for example, its temperature).

As shown in the cross-section shown in FIG. 7, vapor generator body 26 may include a series of passages 38, 40, 42, 44, and 46, for example, circular cylindrical passages. According to aspects of the invention, passages 38, 40, 42, 44, and 46 provide fluid pathways for passing fluids from chambers 32, 34, and 36 to an outlet passage 48 of vapor generator 12. Outlet passage 48 may be directed perpendicular to passages 38, 40, 42, 44, and 46. The vaporous working fluid is discharged from outlet passage 48 to condenser chamber 14. Passages 38, 40, 42, 44, and 46 may typically be machined passages that are capped by plugs 50 (see, for example, FIGS. 1 and 4). Plugs 50 may be conventional plugs, for example, threaded plugs, or specially-designed plugs.

Since vapor generator 12 is typically heated and condenser chamber 14 is typically cooled, as shown in FIG. 6, device 10 may include a thermal insulator 51 mounted between vapor generator 12 and condenser chamber 14. As shown in FIG. 6, insulator 51 may comprise a plate or disk having a through hole that is mounted above outlet passage 48 and about inlet nozzle 86. Insulator 51 may be made from any material that at least partially limits the flow of thermal energy between vapor generator 12 and condenser chamber 14; for example, insulator 51 may be made from a ceramic or plastic, for example, a PTFE plastic, such as, Dupont's Teflon® PTFE or Saint-Gobain's Rulon® PTFE.

In the aspect of the invention shown in FIG. 7, internal chamber 36 may comprise a working fluid chamber having a level of working fluid, for example, FC-72, or internal chamber 36 may contain working fluid injected through port 35, and chamber 32 may be a carrier gas chamber, for example, having ambient air. Chamber 34 may be a reservoir for the working fluid and may be in fluid communication with chamber 36, for example, via wicking material 41; via an internal passage, for example, through a porous medium; or via ports 16 and 18 and external conduits and valves (see FIG. 13). Vaporous working fluid from working fluid chamber 36 and carrier gas from chamber 32 may be selectively combined and then discharged through outlet passage 48. For example, in one aspect, vaporous working fluid from chamber 36 and carrier gas from chamber 32 may be selectively combined to provide a working-fluid-saturated vapor adapted to condense on particles introduced with the sample gas. The combining or mixing of the vaporous working fluid from chamber 36 and carrier gas from chamber 32 may provided by a mixing device 30, for example, a static mixing baffle 30 shown in FIGS. 8 and 9. Mixing device 30 may be positioned in passage 40 in main body 26. As shown in FIG. 7, vaporous working fluid from chamber 36 may be introduced to mixing device 30 via internal passages 42 and 46. For example, passage 42 may be in fluid communication with chamber 36, passage 42 may be in fluid communication with passage 46, and passage 46 may be in fluid communication with passage 40 having mixing device 30. The flow of gas from working fluid chamber 36 to passages 42 and 46 and to mixing passage 40 and mixing device 30 is illustrated by arrow 56 in FIG. 7. Carrier gas from chamber 32 may be introduced to mixing device 30 via internal passages 38 and 46. For example, passage 38 may be in fluid communication with chamber 32, passage 38 may be in fluid communication with passage 46, and passage 46 may be in fluid communication with passage 40. The flow of gas from carrier gas chamber 32 to passage 40 and mixing device 30 is illustrated by arrow 54 in FIG. 7.

Mixing device 30 may comprise any structure that promotes the mixing of the vaporous working fluid with the carrier gas. Mixing device 30 may comprise a rotating device, for example, having one or more mixing vanes or agitators, or a static mixer. In one aspect, mixing device 30 comprises one or more barriers, obstructions, or baffles (such as baffle plates) positioned in passage 40. In another aspect, mixing device 30 may comprise the mixing baffle 30 shown in FIGS. 8 and 9.

FIG. 8 is a perspective view of a mixing baffle 30 according to one aspect of the invention that can be inserted into passage 40 in vapor generating body 26. FIG. 9 is a side elevation view, partially in cross section, of mixing baffle 30 shown in FIG. 8. As shown in FIG. 8, mixing baffle 30 comprises a cylindrical body 62, for example, a circular cylindrical body, though a non-circular cylindrical body may also be used, for instance, a rectangular cylindrical body. Cylindrical body 62 includes a plurality of through holes 64, 66, 68, 70, and 72, for exampled, a plurality of transverse through holes. At least two through holes 64, 66 may be used in mixing baffle 30. As shown in FIGS. 8 and 9, cylindrical body 62 may be provided with one or more recesses 74, 76, 78, and 80 in the outer surface of body 62. Recesses 74, 76, 78, and 80 and the inside surface of passage 40 provide the boundaries of fluid pathways between adjacent through holes 64, 66, 68, 70, and 72 when mixing baffle 30 is inserted within passage 40 in vapor generator body 26. A typical flow path of a mixture of vaporous working fluid and carrier gas from passage 46 (shown in phantom in FIG. 9) through mixing baffle 30 to passage 44 (shown in phantom in FIG. 9) is illustrated by cursive arrow 82 in FIG. 9. As shown in FIG. 7, the flow of mixed gases exits passage 40 and passes through passage 44 to outlet passage 48 as indicated by arrow 84 in FIG. 7.

Figure 6:
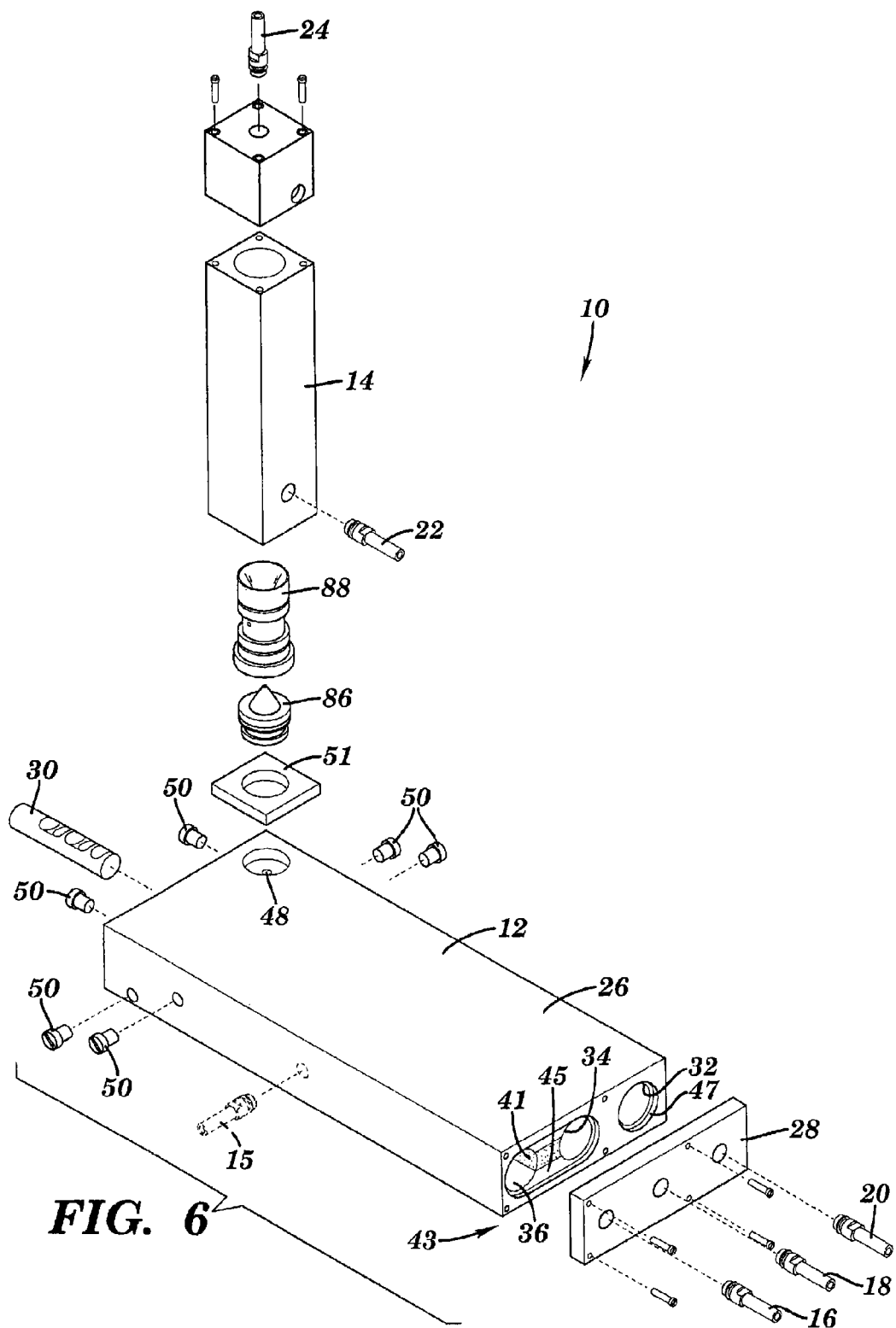
FIG. 6 is an exploded perspective view of the turbulent mixing condensation device shown in FIG. 1.
Figure 7:
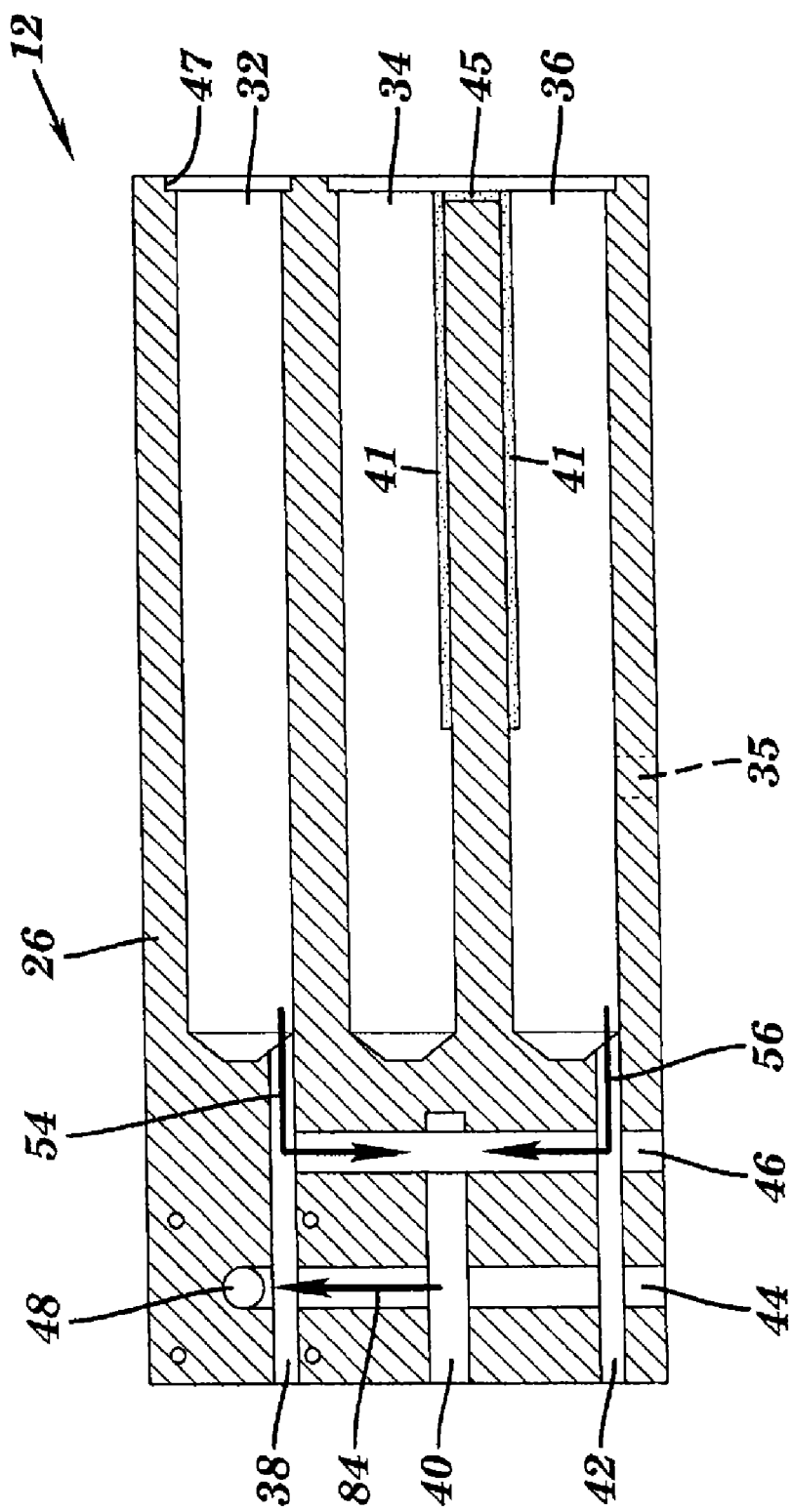
FIG. 7 is a cross sectional view of the vapor generator as viewed along lines 7-7 in FIG. 2 according to one aspect of the invention.
Figure 10:
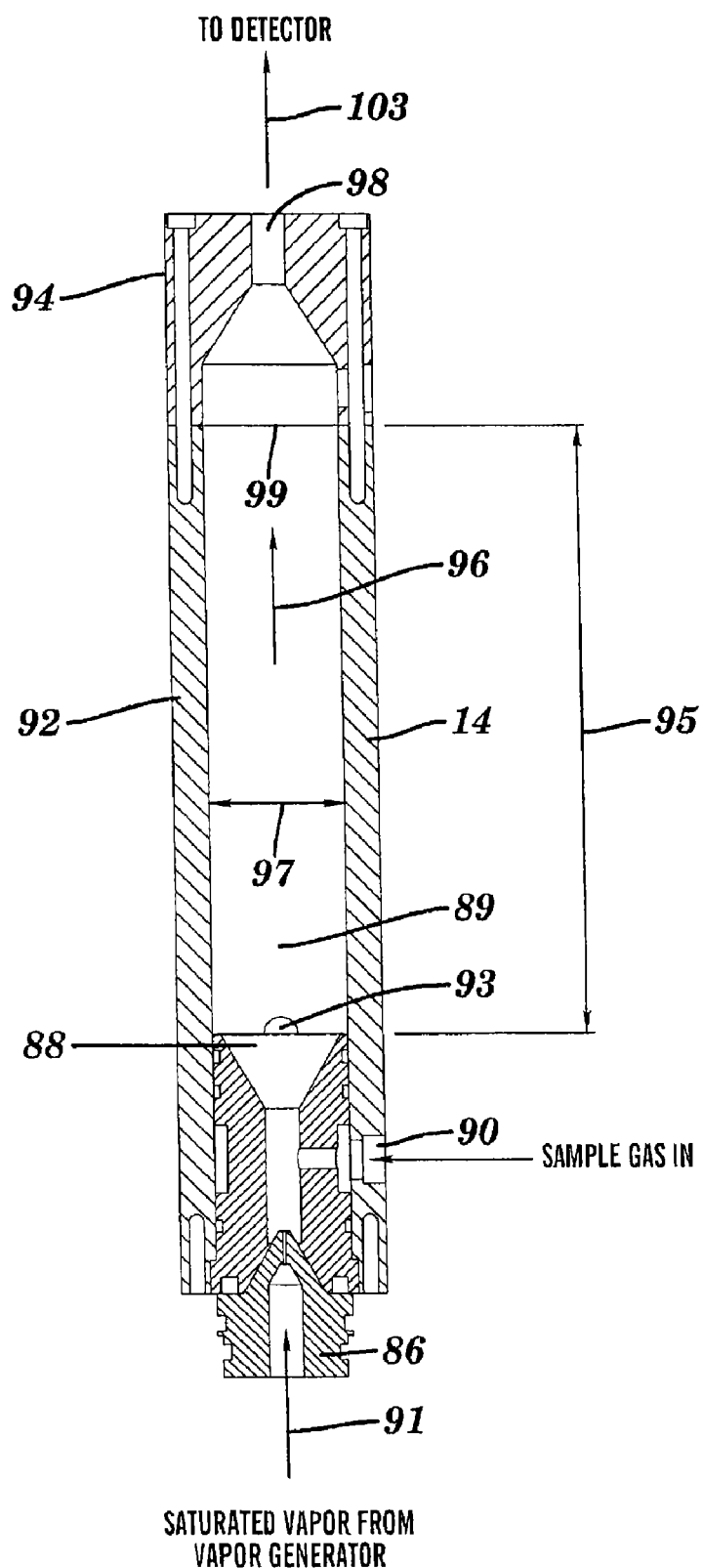
FIG. 10 is a cross-sectional view of a condensation chamber according to one aspect of the invention.

As shown in FIG. 6, after exiting vapor generator 12 via outlet passage 48, the saturated working fluid vapor is directed to condensation chamber 14 through inlet nozzle 86 and mixing insert 88. FIG. 10 is a cross-sectional view of condensation chamber 14 according to one aspect of the invention. As shown in FIG. 10, the saturated working fluid passes through inlet nozzle 86 and sample gas mixing insert 88, where sample gas is introduced via sample gas inlet port 90, before entering the treatment zone 89 of condensation chamber 14. Condensation chamber 14 includes a condensation tube 92 and a condensation tube outlet 94. Inlet nozzle 86 receives the saturated gas stream from vapor generator 12, as indicated by arrow 91, and accelerates and directs the stream into the mixing insert 88. A detailed cross sectional view of nozzle 86 is shown in FIG. 11.

Figure 12:
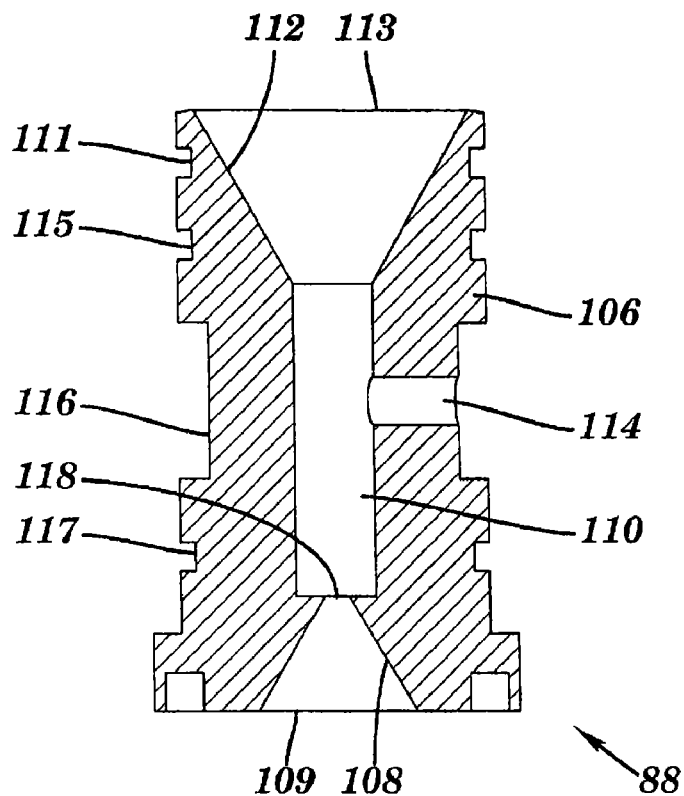
FIG. 12 is a cross-section of a condensation tube sample gas mixing insert according to one aspect of the invention.

Mixing insert 88 provides a means for introducing sample gas to the mixture of carrier gas and working fluid. A detailed cross sectional view of mixing insert 88 is shown in FIG. 12. The sample gas is introduced to mixing insert 88 via at least one sample gas inlet port 90 (FIG. 10), for example, under pressure (for example, pumped) or drawn in due to an under pressure (or vacuum) in condensation chamber 14. Sample gas inlet port 90 typically includes an inlet nozzle, such as nozzle 22 shown in FIG. 1. After introducing the sample gas to the working fluid saturated vapor stream, mixing insert 88 directs the mixed gas stream of sample gas, carrier gas, and working fluid to treatment zone 89 of condensation chamber 14. Condensation tube 92 is adapted, for example, cooled, to promote condensation of the working fluid vapor upon the particles in the combined gas stream. According to conventional condensation nuclei devices, the condensation of the working fluid upon the particles produces enlarged "nuclei" consisting of working fluid condensed on particles that can more readily be detected by conventional particle detection devices. The gas stream having particles with condensed working fluid, as indicated by arrow 96 (FIG. 10) is discharged from condensation chamber 14 via outlet nozzle 94. As indicated by arrow 103, the particle laden gas stream discharged from outlet 94 is directed to a particle detector or counting device (not shown), as will be discussed more fully below with respect to FIG. 13.

Figure 11:
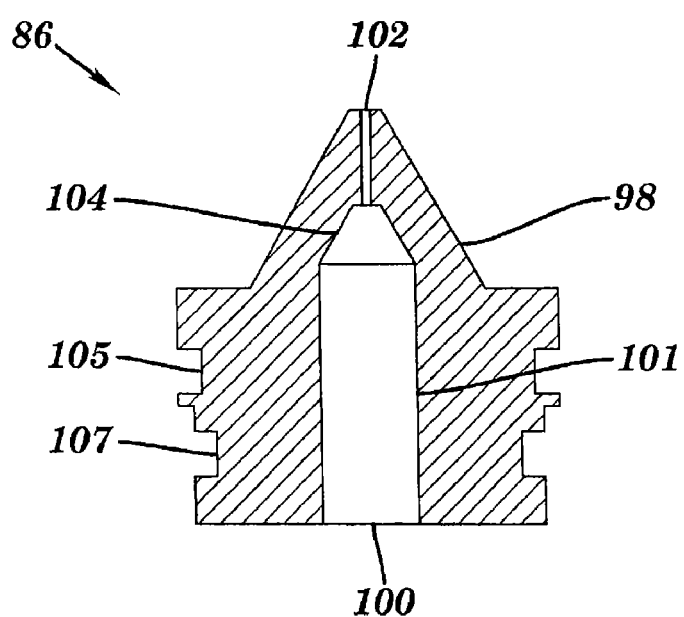
FIG. 11 is a cross section of a condensation tube nozzle according to one aspect of the invention.

FIG. 11 is a cross section of a condensation tube nozzle 86 shown in FIG. 6 according to one aspect of the invention. As shown in FIG. 11, nozzle 86 is a generally axi-symmetric nozzle having a body 98, an inlet 100, an internal passage 101, and an outlet 102. Inlet 100 may comprise the open end of internal passage 101 which may have a diameter ranging from about 0.10 inches to about 1.0 inch. Internal passage 101 may be a cylindrical passage having a length ranging about 0.25 inches to about 2.0 inches. The outlet 102 may comprise an orifice having a diameter of between about 0.005 inches to about 0.10 inches. A flow transition 104 may be present between the internal passage 101 and outlet 102. Transition 104 may be an abrupt transition or a gradual transition, for example, as shown in FIG. 11, the transition 104 may be a conical convergence having an apex angle ranging from 45 degrees to about 90 degrees, for instance, about 60 degrees.

Body 98 may be made from any structural plastic, for example, a polyamide (PA), for example, nylon; a polyamide-imide; a polyethylene (PE); a polypropylene (PP); a polyester (PE); a polytetrafluoroethylene (PTFE); an acrylonitrile butadiene styrene (ABS); a polycarbonate (PC); or a vinyl, such as, polyvinylchloride (PVC), among other plastics; or a metal, for example, from, iron, steel, stainless steel, aluminum, titanium, nickel, magnesium, brass, bronze, or any other structural metal. In one aspect, body 98 may be made from an aluminum alloy, for example, 6061 T6 aluminum alloy. Body 98 of nozzle 86 may be adapted to conform to its mating structures and minimize fluid leakage. For example, body 98 may include appropriate seal accepting cavities, for instance, annular o-ring grooves, 105 and 107, as is conventional.

FIG. 12 is a cross-sectional view of the sample gas mixing insert 88 shown in FIG. 6 according to another aspect of the invention. As shown in FIG. 12, insert 88 is a generally axi-symmetric structure having a body 106, an inlet 108, an internal passage 110, an outlet 112, at least one sample gas inlet 114, and a sample gas annulus 116. Inlet 108 may comprise a convergent transition from a circular opening 109 to the internal passage 110. The diameter of the circular opening 109 in inlet 108 may range from about 0.25 inches to about 2 inches. The convergent transition of inlet 108 may be a conical convergence having an apex angle ranging from 45 degrees to about 90 degrees, for instance, about 60 degrees. In one aspect of the invention, the angle of the conical inlet 108 of insert 88 is substantially the same as the conical shape of nozzle 86 whereby nozzle 86 can be inserted into insert 88. Internal passage 110 may be a cylindrical passage having a length ranging about 0.25 inches to about 2.0 inches and a diameter of about 0.050 inches to about 1 inch. The outlet 112 may comprise a divergent outlet from internal passage 110 to a circular outlet 113. A transition from inlet 108 to internal passage 110 may be gradual or abrupt; for example, inlet 108 may include a gradual convergence to an orifice 118 and then a step change from the diameter of orifice 118 to the diameter of internal passage 110. Orifice 118 may have a diameter ranging from about 0.01 inches to about 0.10 inches. Outlet 112 may comprise a divergence from the diameter internal passage 110 to circular opening 113. The diameter of the circular opening 113 of outlet 112 may range from about 0.25 inches to about 2 inches. The divergent transition of outlet 112 may be a conical convergence having an apex angle ranging from 45 degrees to about 90 degrees, for instance, about 60 degrees.

A sample gas may be introduced to insert 88 through one or more gas inlets 114. Gas inlets 114 may typically receive the sample gas stream from sample gas nozzle 22 shown in FIG. 1 via sample gas inlet port 90 shown in FIG. 10. Insert 88 may include a sample gas annulus 116 provided in the outer diameter of body 106 to assist in distributing the gas flow to the one or more gas inlets 114. In one aspect of the invention, gas inlet 114 may be oriented at any convenient angle with respect to the axis of passage 110 to ensure the introduction of the sample gas to the working-fluid saturated gas into which the sample gas is introduced, for example, at an angle from 30 degrees to about 90 degrees to the axis of passage 110. When inlet 114 is oriented at an angle, it is preferred that at least inlet port 90, and possibly nozzle 22, also be oriented at a similar angle to minimize flow restrictions. In the aspect of the invention shown in FIG. 12, sample gas may be introduced to the working-fluid stream in a direction substantially perpendicular to the axis of passage 110, that is, substantially perpendicular to the flow of the working-fluid gas mixture stream through insert 88.

Body 106 of insert 88 may be made from any structural plastic or metal discussed above with respect to body 98 of nozzle 86. In one aspect, body 106 may be made from a PTFE, for example, from DuPont's Teflon® PTFE or its equivalent. Body 106 of insert 88 may be adapted to conform to its mating structures and minimize fluid leakage. For example, body 106 may include appropriate seal accepting cavities, for instance, annular o-ring grooves, 111, 115, and 117, as is conventional.

Condensation tube 92 is typically cooled by some form of cooling means to promote the condensation of working fluid onto the particles introduced in the sample gas stream. Condensation tube 92 may be cooled by any conventional cooling means, for example, a cooling heat exchanger, for instance, cooling coils or a cooling jacket mounted about condensation tube 92. In one aspect, the temperature of condensation tube 92 may be regulated by using a thermo-electric cooler, for example, a Peltier-type thermo-electric cooler, or its equivalent. During the operation of the present invention, condensation may form on the inside surface of condensation tube 92. In order to isolate and collect this condensation and minimize contamination of the sample gas, as shown in FIG. 10, one or more condensation collecting ports 93 may be provided in condensation tube 92 to collect condensed working fluid. Condensation collecting ports 93 may be located in the vicinity of a condensation collecting dam or annulus, for example, the top edge of insert 88 may act as a collection dam for the condensing fluid flowing down the internal surface of condensation tube 92. In one aspect, this condensed working fluid may be collected and returned to a working fluid supply reservoir, for example, after filtration of the condensed fluid.

With the aid of the assembly shown in FIG. 10, according to one aspect, after passing the working-fluid stream through insert 88 at a first temperature and introducing the sample gas stream via one or more inlets 114 at a second temperature, typically lower than the first temperature, the gas mixture enters treatment zone 89 of condensation tube 92 at a third temperature, lower than the first temperature. Since the working fluid stream is typically saturated with working fluid at the first temperature and the third temperature is typically lower than the first temperature, the gas stream introduced to treatment zone 89 of condensation tube 92 typically comprises a super-saturated gas stream at the third temperature, that is, a gas stream super-saturated with working fluid at the third temperature. According to aspects of the present invention, this super-saturated gas stream is ideal for condensation of the working fluid upon the particles in the mixture of gases exiting insert 88. This condensation is effected in treatment zone 89 of condensation tube 92. In one aspect of the invention, the sample gas stream introduced via inlets 114 is turbulently mixed with the gas mixture, for example, whereby a turbulent flow of gas is introduced to treatment zone 89.

Condensation tube 92 acts as a retention chamber through which the super-saturated, particle-laden gas stream is passed and wherein the working fluid is allowed to condense on the particles in the gas stream to enlarge the particles for subsequent detection. The retention time in treatment zone 89 of condensation tube 92 may range from about 0.25 seconds to about 5.0 seconds and is governed by the dimensions of tube 92, for example, length 95 and inside dimension 97, for instance, a diameter or width, of condensation tube 92 and the velocity of flow through tube 92. The length 95 of condensation tube 92 may vary from about 3 inches to about 36 inches, but is typically between about 3 inches and about 6 inches. The inside diameter 97 of condensation tube 92 may vary from about 0.25 inches to about 6 inches, but is typically between about 0.75 inches and about 1.50 inches.

After passing through condensation tube 92, the gas with enlarged particles having condensed working fluid thereon are discharged from condensation chamber 14 via outlet 94. Outlet 94 includes an inlet 99 and may comprise a convergent geometry that converges to discharge 98. Inlet 99 typically has an inside dimension (that is, diameter or width) about equal to the inside dimension 97 of condensation tube 92, for example, between about 0.25 inches and about 6 inches. Discharge 98 typically has an inside dimension (that is, diameter or width) between about 0.75 inches to about 1.50 inches. Outlet 94 may comprise any flow geometry that transitions the flow of gas from condensation tube 92 to an outlet nozzle, such as nozzle 24 shown in FIG. 1. The outlet nozzle may be directed at any angle with respect to the axial direction of condensation tube 92, for example, the nozzle may be directed perpendicular to the axial direction of condensation tube 92. However, as shown in FIGS. 1-6, in one aspect, the discharge from outlet 94 may be directed substantially parallel to the axial direction of condensation tube 9, for example, substantially parallel to the direction of the flow of gas through condensation tube 92. For instance, the axis of the discharge 98 of outlet 94 may be co-axial with the axis of condensation tube 92.

Figure 13:
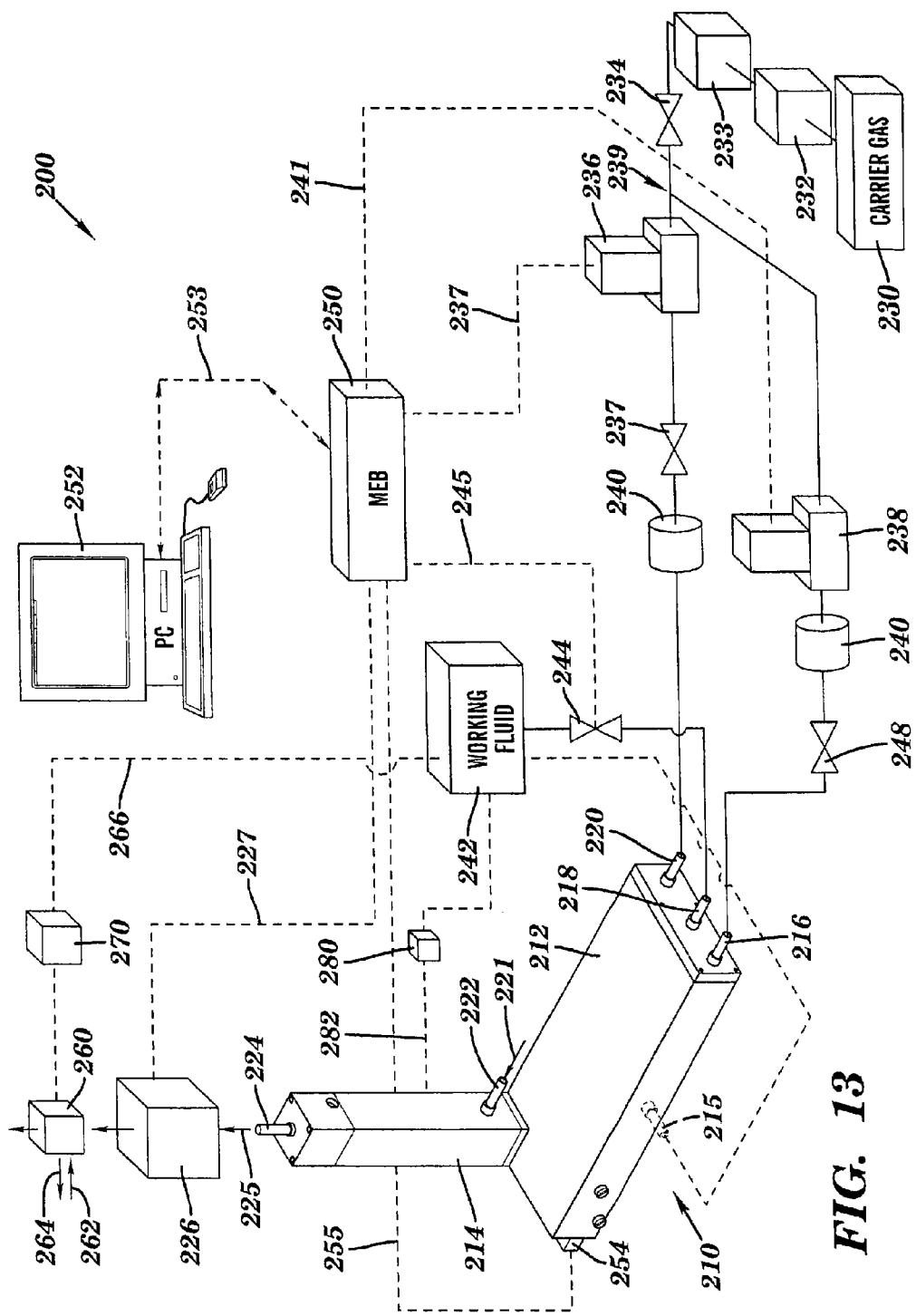
FIG. 13 is a schematic diagram of a condensation nuclei counter system according to another aspect of the invention.

FIG. 13 is a schematic diagram of a condensation nuclei counter system 200 according to another aspect of the invention. System 200 includes a turbulent mixing condensation device 210, for example, similar to device 10 shown in FIGS. 1 through 12, having a vapor generator 212 and a condensation chamber 214. According to aspects of the invention, vapor generator 212 includes inlet ports 216, 218, and 220. Inlet port 216 may be adapted to receive and introduce carrier gas and working fluid to an internal working fluid chamber in vapor generator 212, for example, similar to working fluid chamber 36 shown in FIG. 7. Inlet port 218 may be adapted to receive working fluid into and may discharge working fluid from an internal working fluid reservoir in vapor generator 212, for example, similar to working fluid reservoir 34 shown in FIG. 7. Inlet port 220 may be adapted to receive and introduce carrier gas to an internal carrier gas chamber in vapor generator 212, for example, similar to carrier gas chamber 32 shown in FIG. 7. As described with respect to FIG. 7, the carrier gas introduced via inlet port 220 and the working fluid introduced to inlet port 218 may be mixed in vapor generator 212 to provide a gas having desired saturation ratio and then forwarding the gas to condensation chamber 214.

According to aspects of the invention, condensation chamber 214 receives a sample gas (indicated by arrow 221) having particles via port 222 and discharges a gas having enlarged particles via outlet 224 (indicated by arrow 225) which are forwarded to a particle-detecting device 226, for example, to detect at least one characteristic of the particles.

Particle detecting device 226 may be any particle detecting device adapted to detect at least one characteristic of the particles present in gas stream 225, for example, size (that is, diameter), density, and number. Particle detecting device 226 may be an optical particle counter, such as, an optical particle counter provided by the assignee of this application.

Condensation chamber 214 may include at least one outlet, for example, one or more collecting ports 93 shown in FIG. 10, for collecting working fluid that condenses on the inside surfaces of chamber 214 and forwarding the condensed working fluid in conduit 282 to disposal, storage, or treatment. As shown in FIG. 13, in one aspect, the condensed working fluid in conduit 282 may be returned to working fluid supply 242. A filtering device 280 may be located in conduit 282 to remove any undesirable impurities, for example, particles introduced by the sample gas, from the condensed working fluid.

According to aspects of the present invention, a carrier gas from carrier gas source 230 may be introduced to condensation device 210 through a series of conduits, valves, and flow control and conditioning devices. According to aspects of the invention, the carrier gas may nitrogen, an inert gas, air, or mixtures thereof, among other gases. In one aspect, the carrier gas may be ambient air. The carrier gas may be pressurized, that is, have a super atmospheric pressure, by means of carrier gas pressurizing device 232, for example, a pump or a blower. The carrier gas may be dried and/or cooled by means of a dryer (or dehumidifier) and/or cooler 233. The drying (or dehumidifying) of the carrier gas can minimize or eliminate the potential for moisture (that is, water vapor) or condensed water to interfere with the accuracy and operation of device 210, for example, to avoid water condensation in condensation chamber 214 or on the particles in the sample gas.

In the CNC art, there are primarily two types of CNC devices: conductive cooling type and mixing type. In the conductive cooling type of CNC, such as disclosed by Argarwal, et al. (1979) and Wilson, et al. (1983), the sampled gas containing particles is introduced to the saturation section of the device and exposed to and absorbs at least some working fluid. The sample gas and working fluid are then passed to a condenser section where condensation of working fluid on the particles is promoted, for example, by cooling. In a conductive cooling type CNC, the sample gas and the carrier gas are typically the same gas. If there is any excess water (that is, moisture) in the sample gas, the water may condense onto the sample gas particles and interfere with the condensation of the carrier gas, which can interfere with the measured results. In this case, since the sample gas is the same as the carrier gas, it is difficult to remove moisture, that is, to dry, the carrier gas without losing some sample particles and thus interfering with the intended measurement. Aspects of the present invention overcome this disadvantage of the prior art.

In mixing type CNC devices, such as the present invention, the sample gas stream and the carrier gas stream are separate gas streams. Therefore, removing moisture from the carrier gas stream in aspects of the present invention will not interfere with the particle content of the sample gas stream. For example, passing the carrier gas through dryer 233 may remove at least some moisture from the carrier gas. In one aspect, dryer 233 may remove at least 50% of the moisture in the carrier gas, but may typically remove at least 80%, and possibly at least 90% of the moisture in the carrier gas. In one aspect, of the invention, dryer 233 may be located in the position of filter 240 in system 200. Dryer 233 may be the dryer disclosed in copending U.S. application Ser. No. 11/281,273 filed on Nov. 17, 2005, entitled "A Parallel-Plate Diffusion Gas Dehumidifier and Methods For Use", the disclosure of which is incorporated by reference herein.

The flow of carrier gas may be regulated by one or more flow control devices 234, 236, and 238, for example, device 234 may be a manual isolation valve and devices 236 and 238 may be automated flow or mass control valves. The distribution of carrier gas to ports 216 and 220 may be regulated by control valves 236 and 238 down stream of a tee connection 239. The flow of carrier gas to port 220 may also be regulated by an orifice 237, for example, an orifice referred to as "the critical orifice," that may be designed to limit the maximum flow of carrier gas to the system. Before being introduced to inlets ports 216 and 220, the carrier gas may be passed through filters 240, for example, aerosol filters, to remove any particles or debris that may be present in the carrier gas. In one aspect, in addition to or in lieu of filters 240, a single filter 240 may be located in the carrier gas stream upstream of tee connection 239, that is, before the flow of carrier gas is divided, for example, a filter 240 may be positioned between pump 232 and dryer 233.

According to aspects of the present invention, working fluid, for example, an alcohol or perfluoro compound, may be introduced to condensation device 210 via inlet port 218 from working fluid source 242. The flow of working fluid from source 242 to inlet port 218 may be regulated by flow control device 244, which, like any of the flow control devices disclosed herein, may be a manual or an automated control valve. The operation of flow control device 244, for example, an automated solenoid valve, may be regulated by a level sensor positioned in an internal reservoir chamber in vapor generator 212, for example reservoir chamber 34 in FIG. 7. According to one aspect of the invention, the working fluid passed to port 218 introduces working fluid to an internal working fluid reservoir in vapor generator 212 where the reserve working fluid may be maintained at temperature, for example, between about 20 degrees C. and about 45 degrees C. This working fluid may then be introduced at temperature to the working fluid chamber in vapor generator 212. For example, in one aspect of the invention, the internal chamber associated with port 218, such as chamber 34 in FIG. 7, and the internal chamber associated with port 216, such as chamber 36 in FIG. 7, may be in fluid communication via an absorbent wicking material, for example, a wicking material 41 shown in and described with respect to FIGS. 6 and 7.

In another aspect, should the level of working fluid in the working fluid chamber in vapor generator 212 fall below a predetermined level, for example, as detected by a level sensor (not shown), working fluid at substantially the same temperature of the working fluid in the working fluid chamber, may be passed from the working fluid reservoir out of port 218 to port 216 (through conduits not shown) and to the working fluid chamber.

In one aspect, condensation device 210 may comprise a vapor generator 212 having at least one inlet nozzle 215 (shown in phantom) for injecting working fluid into an internal chamber of vapor generator 212. As discussed above with respect to FIG. 7, the injection of working fluid into vapor generator 212 may supplement or replace the function of introducing working fluid via ports 216 or 218. The injection of flow, for example, the rate of flow, through nozzle 215 may be varied or regulated, for example, by a controller, in response to a desired saturation level.

In another aspect of the invention, system 200 includes means for recovering and re-using at least some of the working fluid. For instance, system 200 may include a working fluid recovery device or system 260 located downstream of particle-detecting device 226. For example, working fluid recovery system 260 may be a condensing device, for example, any device adapted to cool the flow of gas out of particle-detecting device 226 whereby at least some of the working fluid condenses and can be collected. In one aspect, working fluid recovery system 260 may comprise a thermoelectric cooler in thermal communication with at least one surface over which the gas from particle-detecting device 226 flows which can be cooled. Working fluid recovery system 260 may comprise a heat exchanger having coolant inlet conduit 262 and coolant outlet conduit 264. In addition to the recovery of the uncondensed working fluid, working fluid recovery system 260 may also recover the working fluid that condensed on the aerosol particles. For example, fluid recovery system 260 may include a condensing device and a filtering device to remove at least some particles from the condensed liquid.

In one aspect, fluid recovery system 260 may recover at least 50% of the working fluid used in system 200, but may typically recover at least 80%, and possibly at least 90% or 95%, or even approach 98% of the working fluid in the carrier gas. The recovery system 260 may recover substantially all the working fluid (that is, substantially 100%) whereby little or no working fluid is released to the environment.

The recovered working fluid may be forwarded to disposal, storage, or treatment. As shown in FIG. 13, the recovered working fluid may be collected and forwarded to the working fluid supply 242, for example, via conduit 266, for recycling or reuse. The recovered working fluid may be filtered, for example, by means of filtering device 270 positioned in conduit 266, to remove any undesirable impurities, for example, particles introduced by the sample gas.

By recovering at least some of the working fluid (preferably substantially all the working fluid) according to aspects of the invention, little or no working fluid is released to the environment. In addition to minimizing or preventing any impact upon humans, flora, fauna, water, or air, by recovering the working fluid, little or no working fluid can contaminate the sampled gas stream. In addition, some working fluids, such as the perfluourinated compounds mentioned above, are expensive. Therefore, recovery and reuse of these compounds using aspects of the present invention can be much more cost effective than conventional CNC systems without working fluid recovery. Aspects of the present invention make the use of such perfluourinated compounds economically and/or environmentally feasible.

The operation and control of system 200 may be regulated by an automated control system, for example, by means of a controller 250 and an accompanying user interface 252 connected via electrical connection 253. Controller 250 may, for example, a conventional control device, for instance, a personal computer operating control software. Controller 250 is typically adapted to receive data and/or transmit data and control signals to and from conventional control and monitoring devices. The electrical signals transmitted from or received by controller 250 may be 0-1 VDC signals or 4-20 mA signals, as is conventional. Controller 250 may regulate and control the flow of carrier gas (for example, for saturation scanning) by controlling the operation of valves 236 via electrical connection 237 and valve 238 via electrical connection 241. Controller 250 may regulate and control the flow of working fluid from source 242 by controlling the operation of valve 244 via electrical connection 245. The temperature of the saturated gas stream exiting vapor generator 212 or the temperature of vapor generator 212 may be detected by one or more temperature sensors located in or on vapor generator 212, for example, temperature sensor 254, which may, for example, be a thermocouple or resistive thermal device (RTD), monitored by controller 250 via electrical connection 255. Controller 250 may also receive data and control signals from and transmit data and signals to particle-detecting device 226 via electrical connection 227.

According to aspects of the present invention, system 200 may be operated to effectively detect the size of particles in an aerosol gas stream 221 introduced to inlet 222. This detection may be performed substantially continuously or substantially intermittently. System 200 may be portable and transportable to a location at which ambient air sampling may be monitored. In another aspect of the invention, system 200 may be dedicated to a specific location, for example, a residence or a commercial site, for example, a laboratory or clean room, among other sites at which air quality may be monitored.

System 200 may be positioned at a location where ambient air quality is to be monitored for particle content. Prior to operation, the working fluid reservoir in vapor generator 212 may be filled by directing working fluid from working fluid source 242 through valve 244 and inlet port 218 and into the working fluid reservoir, for example, similar to the working fluid reservoir 34 shown in FIG. 7. Then, the working fluid chamber in vapor generator 212 may be at least partially filled with working fluid to provide a level of working fluid in the working fluid chamber, such as, working fluid chamber 36 in FIG. 7. The working fluid may be passed from source 242 inlet port 216 and to a working fluid chamber. When sufficient working fluid is provided, the vapor generator 212 may be heated to operating temperature, for example, to at least about 35 degrees C., by a heating means (not shown), for example, by means of a heat exchanger or heating jacket. The temperature of vapor generator 212 may be monitored and controlled via temperature sensor 254.

The temperature of the condensation chamber 214 may also be regulated. For example, the temperature of condensation tube 92 of condensation chamber 214 may be maintained at a temperature of about 20 degrees C. to enhance the condensation of the working fluid onto the particles. The temperature of the condensation chamber 214 may be regulated by a cooling jacket mounted to condensation chamber 214 through which a cooling medium, such as water, may be passed. The regulation of the temperature of vapor generator 212 and condensation tube 92 may be monitored and controlled by controller 250 with appropriate temperature sensors and electrical connections, as is conventional.

When the vapor generator 212, the working fluid, and the condensation chamber 214 are at their respective desired operating temperatures. Aerosol sampling may commence by introducing carrier gas from source 230, for example, ambient air, to the condensation device 210. In one aspect, carrier gas may be pressurized by pump 232 to at least about 5 psig. The flow of carrier gas to device 210 is regulated by valves 236, 238 and orifice 237. The carrier gas introduced to inlet port 220 passes through the carrier gas chamber (for example, chamber 32 in FIG. 7) and into the static mixing baffle (for example, baffle 30, as shown by arrow 54 in FIG. 7). At substantially the same time, the carrier gas introduced to port 216 passes through the working fluid chamber (chamber 36 in FIG. 7) evaporates and absorbs working fluid from the surface of the working fluid in the working fluid chamber. The working fluid containing carrier gas is then passed into the static mixing baffle 30 (as shown by arrow 56 in FIG. 7). The carrier gas and working fluid containing carrier gas are mixed by baffle 30 to produce a carrier gas having a specific "saturation ratio" (see below) at a first temperature, for example, at a temperature of about 35 degrees C.

The substantially mixed carrier gas and working fluid is then introduced to the condensation chamber 214, as most clearly shown in FIG. 10. The carrier gas and working fluid is first introduced to nozzle 86 and directed by the orifice 102 in nozzle 86 to insert 88. While passing through insert 88, the aerosol 221 having particles is introduced to nozzle 222 at a second temperature, lower than the first temperature, for example, at about the prevailing ambient air temperature (for example, at a temperature of between about 15 and 25 degrees C.) to produce a working fluid/carrier gas/aerosol-with-particles mixture at a third temperature, lower than the first temperature. The third temperature is typically a function of the volume and temperature of the carrier gas and working fluid and the volume and temperature of the sampled aerosol gas 221. The introduction of aerosol 221 may typically be practiced turbulently, for example, whereby a turbulent mixture of aerosol 221, carrier gas, and working fluid is provided. According to aspects of the invention, the mixture of gases at the third temperature is then introduced to condensation tube 92, for example, again, typically, turbulently introduced. Condensation tube 92 is typically maintained at a fourth temperature, lower than the third temperature, for example, at about 3 to about 10 degrees C., typically, about 5 degrees C., whereby the working fluid, carrier gas and aerosol gas mixture becomes saturated or even supersaturated with working fluid. According to the known art, the saturated gas mixture promotes condensation of the working fluid upon the particles in the gas mixture whereby the particles introduced with the aerosol gas are enlarged. The gas mixture with enlarged particles is then discharged from outlet port 224 to particle detecting device 226 as indicated by arrow 225.

Particle detecting device 226 then detects at least one characteristic of the enlarged particles, for example, their number, as is conventional. Typical characteristics or parameters of the aerosol particles that may be detected according to aspects of the invention include size (that is, diameter) and density. The characterizing data may be stored be detecting device 226 for later retrieval and analysis or the characterizing data may be forwarded to user interface 252 via electrical connection 227 and controller 250.

In one aspect of the invention, the flow of carrier gas to the condensation device 210 may be maintained relatively constant whereby the extent of saturation of the carrier gas introduced to the condensation chamber 214 may be substantially constant. In another aspect of the invention, the flow of carrier gas to condensation device 210 may be varied whereby the extent of saturation of the carrier gas introduced to the condensation chamber 214 may be varied. The flow of carrier gas through the carrier gas chamber in condensation device 210 may be varied or the flow of carrier gas to the working fluid chamber may be varied. As a result, the degree of saturation of the gas introduced to condensation chamber 214 may be varied. As noted above, the degree of saturation may also be varied by varying the flow of working fluid into vapor generator 212 through nozzle 215. According to one aspect of the invention, the varying of the saturation of the gas introduced to the condensation chamber 214 may be used to vary the size or nature of the particles detected. In one aspect of the invention, this "saturation scanning" may be effected to vary or scan a characteristic of the particles introduced to condensation device 210. Typical characteristics or parameters of the aerosol particles that may be scanned according to aspects of the invention include size (diameter) and number. For example, scanning may comprising varying the size of the particles detected and then counting the number of particles at each size, or size range.

According to one aspect of the invention, a method and system are provided for detecting a characteristic of particles of varying size in a sample gas. For example, aspects of the invention permit the operator to vary the operating conditions of the method or system and thus vary the size of the particles upon which the working fluid condenses. In this way, the operator can determine one or more characteristics of particles of varying size. The variation in the particle size detection is effected by varying the saturation ratio of the vapor discharged from the vapor generator 212. As recognized in the art, the "saturation ratio," S, of a vapor stream is provided by Equation 1:

$$S=P/P_{sat}(T) \qquad \text{Equation 1.}$$

In Equation 1, P is the pressure of the gas (for example, in units of psi, atmosphere, or kPa) and $P_{sat}(T)$ is the saturation vapor pressure of the gas (in corresponding pressure units) at temperature T. The variation of the saturation ratio may be effected by various means. In prior art CNC devices, the saturation ratio of the gas passing through the condensation chamber is typically substantially fixed. This is due to the practice of operating the prior art devices with substantially fixed carrier gas flows and fixed sample gas flows and at substantially fixed temperatures. In contrast to the prior art, in one aspect, the saturation ratio of the gas passing through the condensation chamber 214 may be varied as desired. Specifically, according to aspects of the present invention, the saturation ratio may be varied whereby the size of the particles enlarged by the device may be varied and the characteristics of particles of varying size can be detected.

The variation of saturation ratio of the vapor during condensation may be effected by varying the flow of carrier gas to the saturation chamber, for example, carrier gas chamber 36 in FIG. 7, or the flow of carrier gas to the working fluid chamber, for example, chamber 32, in FIG. 7, or varying the flow to both chambers. As a result, the saturation ratio of the gas introduced to the condensation chamber, for example, condensation chamber 14 in FIG. 1 will vary. For example, reducing the flow rate of carrier gas to the two chambers may decrease the saturation ratio of the gas in the condensation tube, or increasing the flow rate of carrier gas to the two chambers may increase the saturation ratio of the gas in the condensation tube. In one aspect of the invention, the total flow carrier gas to the two chambers may be kept relatively constant, but the ratio of the flows to each chamber may vary. By maintaining the total flow of carrier gas to the two chambers relatively constant, the flow of sample gas 221 into nozzle 222, for example, due to aspiration, may be relatively constant. Then, by varying the ratio of the carrier gas charged to the carrier gas chamber to the flow of carrier gas to the working fluid chamber, the saturation ratio of the resulting gas mixture, and the size of the particles enlarged, can be varied. For example, for a total carrier gas flow to the carrier gas chamber and working fluid chamber of 2.0 liters/min (L/m), the flow to each chamber may be evenly divided, that is, 1 L/m each to provide a first saturation ratio. The flow of carrier gas to the carrier gas chamber may then be increased to 1.2 L/m and the flow of carrier gas to the working fluid chamber may be decreased to 0.8 L/m, that is, while maintaining the total flow of 2 L/m, to produce a second saturation ratio, typically, less than the first saturation ratio. These numbers are provided for example only, actual flows to the chambers may vary accordingly to provide the desired saturation ratio or saturation ratio scanning.

The variation of the saturation ratio in turn varies the minimum detectable particle size. For example, by using compressed air, at about 5 psig or less, provided by, for example, gas pressurizing device 232, and the two flow controllers 236 and 238, the total flow of carrier gas can be fixed, and the flow of carrier gas to the carrier gas chamber (chamber 36 in FIG. 7) and to the working fluid chamber (chamber 32 in FIG. 7) of vapor generator 212 can be varied to provide the desired saturation ratio.

In another aspect of the invention, the variation in the saturation ratio of the gas during condensation may be effected by varying the rate of flow of working fluid injected into the saturation chamber, for example, varying the rate of flow of working fluid into chamber 36 in FIG. 7 through nozzle 15 or 215. According to this aspect of the invention, condensation device 210 may include only a single chamber 36 into which carrier gas is introduced via nozzle 16 or 216 and into which working fluid is injected through nozzle 15 or 215 to effect a desired saturation ratio. Other means of varying the saturation ratio may be provided, as will be recognized by those skilled in the art.

Aspects of the present invention provide improved methods and devices for detecting particles in aerosol gas streams, for example, in laboratory, clean room, or ambient air gas streams. The methods and devices employ improved turbulent mixing condensation nuclei counter (TMCNC) devices having improved detection ranges and detection efficiencies that surpass those of existing prior art methods and devices. These devices may be used as stand alone units having robust design, consistent and reproducible performance, greater ease of use, and employ a working fluid that is less offensive and less dangerous to humans.

While several aspects of the present invention have been described and depicted herein, alternative aspects may be provided by those skilled in the art to accomplish the same objectives. Accordingly, it is intended by the appended claims to cover all such alternative aspects as fall within the true spirit and scope of the invention.

The invention claimed is:

1. A method for detecting a characteristic of particles in a sample, the method comprising:
    passing a first stream of a carrier gas over a working fluid wherein the carrier gas absorbs at least some of the working fluid to provide a vapor containing working fluid;
    mixing the vapor containing working fluid with a second stream of carrier gas to produce a mixture of working fluid and carrier gas at a first temperature;
    introducing the sample gas to the mixture, the sample gas containing particles and having a second temperature lower than the first temperature, to produce a particle-containing gas having a third temperature lower than the first temperature;
    condensing at least some of the working fluid in the particle-containing gas on to at least some of the particles to produce enlarged particles; and
    detecting the characteristic of at least some of the enlarged particles.

2. The method as recited in claim 1, wherein the method further comprises providing a carrier gas chamber, and wherein passing a first stream of carrier gas over the working fluid comprises passing the first stream from the carrier gas chamber over the working fluid.

3. The method as recited in claim 1, wherein mixing the vapor containing working fluid with a second stream of carrier gas comprises statically mixing the vapor containing working fluid with a second stream of carrier gas.

4. The method as recited in claim 1, wherein condensing comprises introducing the particle-containing gas to a condenser.

5. The method as recited in claim 1, wherein passing the first stream of the carrier gas over the working fluid comprises injecting the working fluid into the first stream of the carrier gas.

6. The method as recited in claim 5, wherein injecting comprises providing one of a fine jet and a fine mist of working fluid.

7. The method as recited in claim 5, wherein the method further comprises varying an injection rate of working fluid to vary a degree of working fluid saturation.

8. The method as recited in claim 1, wherein the mixture of working fluid and carrier gas comprises a first mixture having a first saturation ratio; and wherein introducing the sample gas to the mixture comprises introducing the sample gas to the first mixture; and wherein condensing at least some of the working fluid to produce enlarged particles comprises condensing working fluid onto at least some particles having a first size to produce first enlarged particles; and wherein detecting a characteristic comprises detecting a characteristic of at least some of the first enlarged particles; and wherein the method further comprises:
    introducing the working fluid to the carrier gas to provide a second mixture of working fluid and carrier gas having a second saturation ratio, different from the first saturation ratio;
    introducing the sample gas to the second mixture to produce a second particle-containing gas;
    condensing at least some of the working fluid from the second particle-containing gas onto at least some of the particles in the sample gas stream having a second size, different from the first size, to produce second enlarged particles; and
    detecting the characteristic of at least some of the second enlarged particles.

9. The method as recited in claim 8, wherein the method further comprises controlling the flow of the first stream of carrier gas and the second stream of carrier gas to produce the first saturation ratio.

10. The method as recited in claim 1, wherein the method further comprises regulating saturation of the mixture by the controlling the flow of the first stream of carrier gas and controlling the flow of the second stream of carrier.

11. The method as recited in claim 10, wherein regulating saturation of the working-fluid-saturated vapor comprises varying the saturation of the mixture from a first degree of saturation to a second degree of saturation.

12. The method as recited in claim 1, wherein the method further comprises, prior to passing the first stream of carrier gas over the working fluid, drying the first stream of carrier gas to remove at least some moisture from the first stream of carrier gas.

13. The method as recited in claim 12, wherein drying comprising removing at least 80% of the moisture from the first stream of the carrier gas.

14. The method as recited in claim 1, wherein the method further comprises providing a level of working fluid in a working fluid chamber and wherein passing a first stream of carrier gas over the working fluid comprises passing the first stream of carrier gas through the working fluid chamber.

15. The method as recited in claim 14, wherein the method further comprises maintaining the level in the working fluid chamber.

16. The method as recited in claim 1, wherein the method further comprises providing a working fluid reservoir and wherein maintaining the level in the working fluid chamber comprises supplying working fluid from the working fluid reservoir to the working fluid chamber.

17. The method as recited in claim 16, wherein the method further comprises maintaining the working fluid chamber and the working fluid reservoir at about the same temperature.

18. The method as recited in claim 1, wherein the method further comprises, recovering at least some of the working fluid from the carrier gas.

19. The method as recited in claim 18, wherein recovering at least some working fluid comprises recovering at least 80% of the working fluid.

20. The method as recited in claim 18, wherein recovering at least some of the working fluid from the carrier gas comprises recovering at least some of the working fluid from at least one of the gas in the particle-containing gas and the enlarged particles in the particle-containing gas.

21. The method as recited in claim 18, wherein recovering at least some of the working fluid from the carrier gas comprises recovering at least some of the working fluid by passing the carrier gas in heat exchange relationship with a cooler fluid.

22. The method as recited in claim 21, wherein the method further comprises re-using the recovered working fluid as a source of working fluid.

23. The method as recited in claim 1, wherein the method further comprises filtering the recovered working fluid to remove at least some particles from the recovered working fluid.

\* \* \* \* \*